United States Patent [19]

Davidson

[11] Patent Number: 5,434,058
[45] Date of Patent: Jul. 18, 1995

[54] APOLIPOPROTEIN B MRNA EDITING PROTEIN COMPOSITIONS AND METHODS

[75] Inventor: Nicholas O. Davidson, Olympia Fields, Ill.

[73] Assignee: Arch Development Corporation, Chicago, Ill.

[21] Appl. No.: 158,682

[22] Filed: Nov. 24, 1993

Related U.S. Application Data

[63] Continuation-in-part of Ser. No. 15,203, Feb. 9, 1993.

[51] Int. Cl.$^6$ .......................... C12N 5/00; C12N 9/22; C12P 21/06; C07H 19/00
[52] U.S. Cl. .................................. 435/69.1; 435/199; 435/240.2; 435/320.1; 536/22.1; 536/23.1; 536/23.2; 536/23.5
[58] Field of Search .................... 435/69.1, 199, 240.2, 435/320.1; 536/22.1, 23.1, 23.2, 23.5

[56] References Cited

PUBLICATIONS

Glover "Principles of Cloning DNA" *Gene Cloning* pp. 1–20 1984.
Beisiegel et al., The LDL-receptor-related protein, LPR, is an apolipoprotein E-binding protein, *Nature*, 341:162–164, 1989.
Bostrom et. al, Apolipoprotein B mRNA Editing: Direct Determination of the Edited Base and Occurrence in Non-Apolipoprotein B-Producing Cell Lines, *J. Bio. Chem.*, 265:22446–22452, 1990.
Bradford, M. M., A Rapid and Sensitive Method for the Quantitation of Microgram Quantities of Protein Utilizing the Principle of Protein–Dye Binding, *Analytical Biochem.*, 72:248–254, 1976.
Chan et. al, The Human Apolipoprotein B-100 Gene: A Highly Polymorphic Gene That Maps To The Short Arm of Chromosome 2, *Biochem. Biophys. Res. Comm.*, 133:248–255, 1985.
Chen et al., RNA Editing of Apolipoprotein B mRNA, *J. Biol. Chem.*, 265:6811–6816, 1990.
Chen et. al, Apolipoprotein B–48 Is the Product of a Messenger RNA with an Organ-Specific In-Frame Stop Codon, *Science*, 238:362–366, 1987.
Chen et. al, The Complete cDNA and Amino Acid Sequence of Human Apolipoprotein B-100*, *J. Biol. Chem.*, 261:12918–12921, 1986.
Cladaras et. al, The complete sequence and structural analysis of human apolipoprotein B-100: relationship between apoB-100 and apoB-48 forms, *EMBO J.*, 5:3495–3507, 1986.
Coleman et. al, Developmental coordinate expression of triacylglycerol and small molecular wight apoB synthesis and secretion by rat hepatocytes, *J. Lipid Res.*, 28:33–42, 1988.
Demmer et. al, Tissue–specific expression and developmental regulation of the rat apolipoprotein B gene, *Proc. Natl. Acad. Sci. USA*, 83:8102, 1986.
Driscoll et al., Induction of RNA Editing at Heterologous Sites by Sequences in Apolipoprotein B mRNA, *Mole. Cell. Bio.*, 13:(12)7288–7294, 1993.
Driscoll and Casanova, Characterization of the Apolipoprotein B mRNA Editing Activity in Enterocyte Extracts, *J. Biol. Chem.*, 265:21401–21403, 1990.
Driscoll et. al, An In Vitro System for the Editing of Apolipoprotein B mRNA, *Cell*, 58:519–525, 1989.
Edwards et. al, Oligodeoxyribonucleotide ligation to single-stranded cDNAs: a new tool for cloning 5'ends of mRNAs and for constructing cDNA libraries in vitro amplification, *Nucleic Acids Res.*, 19:5227, 1991.
Felgner, R. L. and Rhodes, G., Gene Therapeutics, *Nature*, 349:351–352, 1991.

(List continued on next page.)

*Primary Examiner*—Robert A. Wax
*Assistant Examiner*—Hyosuk Kim
*Attorney, Agent, or Firm*—Arnold, White & Durkee

[57] ABSTRACT

The present invention provides a protein that edits apo B RNA. A polynucleotide that comprises a DNA sequence that encodes an apo B RNA editing protein and an expression vector comprising such a polynucleotide are also provided. Processes for producing an apo B RNA editing protein, editing apo B RNA and altering apo B protein production are also provided.

9 Claims, 5 Drawing Sheets

OTHER PUBLICATIONS

Frohman, M. A. and Martin, G. R., Cut, Paste, and Save: New Approaches to Altering Specific Genes in Mice, *Cell*, 56:145–147, 1989.

Frohman et. al, Rapid production of full-length cDNAs from rare transcripts: Amplification using a single gene-specific oligonucleotide primer, *Proc. natl. Acad. Sci. USA*, 85:8998–9002, 1988.

Garcia et al., Characterization of Apolipoprotein B mRNA Editing From Rabbit Intestine, *Arteriosclerosis*, 12:172–179, 1991.

Giannoni et al., Complementation of Apolipoprotien B mRNA Editing by Human Liver Accompanied by Secretion of Apolipoprotein B48, *J. Biol. Chem.*, 269:(0)1–5, 1994.

Greeve et al., Apolipoprotein B mRNA editing in 12 different mammalian species: hepatic expresssion is reflected in low concentrations of apoB-containing plasma lipoproteins, *J. Lipid Research*, 34:1367–1383, 1993.

Hardman et al., Structural comparison of Human Apolipoproteins B–48 and B–100, *Biochemistry*, 26:5478–5486, 1987.

Hatzoglou et al., Hepatic Gene Transfer in Animals Using Retroviruses containing the Promoter from the Gene for Phosphoenolpyruvate Carboxykinase, *J. Biol. Chem.*, 17285–17292, 1989.

Herz et al., Surface location and high affinity for calcium of a 500–kd liver membrane protein closely related to the LDL-receptor suggest a physiological role as lipoprotein receptor, *EMBO J.*, 7:4119–4127, 1988.

Hodges, P. and Scott, J., Apolipoprotein B mRNA editing: a new tier for the control of gene expression, *Trends Biochem.*, 17:77–81, 1992.

Hopkins et. al, Identity of cells containing apolipoprotein B messenger RNA, in 6— to 12— week postferilization human embryos, *Development*, 100:83–93, 1987.

Hospattankar et al., Identification of a Novel In–Frame Translational Stop Codon in Human Intestine ApoB mRNA, *Biochem. Biophys. Res. Comm.*, 148:(1)279–285, 1987.

Huber et al., Retroviral–mediated gene therapy for the treatment of hepatocellular carcinoma: An innovative approach for cancer therapy, *Proc. Natl. Acad. Sci. USA*, 88:8039–8043, 1991.

Innerarity et al., Structural Relationship of Human Apolipoprotein B48 to Apolipoprotein B100, *J. Clin. Invest.*, 80:1794–1798, 1987.

Jiao et al., Editing of apolipoprotein B messenger RNA in differentiated Caco-2 cells, *J. Lipid Res.*, 31:695–700, 1990.

Kayano et al., Human Facilitative Glucose Transporters, *J. Biol. Chem.*, 265:(22)13276–13282, 1990.

Knott et al., Complete protein sequence and identification of structural domains of human apolipoprotein B, *Nature*, 323:734–738, 1986.

Kyte, J. and Doolittle, F., A Simple Method for Displaying the Hydropathic Character of a Protein, *J. Mol. Biol.*, 157:105–132, 1982.

Lau et al., Apolipoprotein B mRNA Editing Is an Intranuclear Event That Occurs Posttranscriptionally Coincident with Splicing and Polyadenylation, *J. Biol. Chem.*, 266:(30)20550–20554, 1991.

Lau et al., 40 kilodalton rat liver nuclear protein binds specifically apolipoprotein B mRNA around the RNA editing site, *Nucleic Acids Res.*, 18:(19)5817–5821, 1991.

Li et al., The apolipoprotein multigene family: biosynthesis, structure, structure-function relationships, and evolution, *J. Lipid Res.*, 29:245–271, 1988.

Ludwig et al., DNA Sequence of the Human Apolipoprotein B Gene, *DNA*, 6:(4)363–372, 1987.

Luo, C., and Li, W., Structure and Evolution of the Apolipoprotein Multigene Family, *J. Mol. Biol.*, 187:325–340, 1986.

Mehrabian et al., Human Apolipoprotein B: Chromosomal Mapping and DNA Polymorphisms of Hepatic and Intestinal Species, *Somatic Cell and Molecular Genetics*, 12:(3)245–254, 1986.

Navaratnam et al., The p27 Catalytic Subunit of the Apolipoprotein B mRNA Editing Enzyme Is a Cytidine Deaminase, *J. Biol. Chem., 268:(28)20709–20712, 1993*.

Powell et al., A Novel form of Tissue-Specific RNA Processing Produces Apolipoprotein-B48 in Intestine, *Cell*, 50:831–840, 1987.

Ranade, V. V., Drug Delivery Systems. 1. Site-Specific Drug Delivery Using Liposomes as Carriers, *J. Clin. Pharmacol*, 29:685–694, 1989.

Seishima et al., Regulation of hepatic apolipoprotein synthesis in the 17 x-ethinyl estradiol–treated rat, *J. Lipid Res.*, 32:941–951, 1991.

(List continued on next page.)

OTHER PUBLICATIONS

Shah et al., Sequence Requirements for the Editing of Apolipoprotein B mRNA, *J. Biol. Chem.*, 266:(25)16301–16304, 1991.

Smith et al., *In Vitro* apolipoprotein B mRNA editing: Identification of a 27S editing complex, *Proc. Natl. Acad. Sci. USA*, 88:1489–1493, 1991.

Sumikawa et al., Separate fractions of mRNA from *Torpedo* electric organ induce chloride channels and acetylcholine receptors in *Xenopus* oocytes, J. EMBO, 3:2291–2294, 1984.

Teng et al., Apolipopotein B Messenger RNA Editing Is Developmentally Regulated In Pig Small Intestine: Nucleotide Comparison of Apolipoprotein B Editing Regions In Five Species, *Biochem. Biophys. Res. Comm.*, 173:(1)74–80, 1990.

Teng et al., Apolipoprotein B Messenger RNA Editing Is Developmentally Regulated and Widely Expressed in Human Tissues, *J. Biol. Chem.*, 265:(33)20616–20620, 1990.

Teng et al., Molecular Cloning of an Apolipoprotein B Messenger RNA Editing Protein, *Science*, 260:1816–1819, 1993.

Teng and Davidson, Evolution of Intestinal Apolipoprotein B mRNA Editing, *J. Biol. Chem.*, 267:(29)21265–21272, 1992.

Teng and Davidson, Chick Apolipoprotein B (Apo B) mRNA Is Not Entitled, but Chick Enterocyte contains Protein Factor(s) Which Bind and Enhance Editing of Heterologous ApoB RNAs, *Arteriosclerosis and Thrombosis*, 11(5):1402a, 1991.

Weatherall, D. J., Gene Therapy In Perspective, *Nature*, 349:275–276, 1991.

Wu et al., Apolipoprotein B mRNA Editing: Validation of a Sensitive Assay and Developmental Biology of RNA Editing in the Rat, *J. Biol. Chem.*, 265:(21)12312–12316, 1990.

Yang et al., Sequence, structure, receptor-binding domains and internal repeats of human apolipoprotein B-100, *Nature*, 323:738–742, 1986.

Zwiebel et al., High-Level Recombinant Gene Expression in Rabbit Endothelial Cells Transduced by Retroviral Vectors, *Science*, 243:220–222, 1989.

```
                                                        1
                                                        Met Ser Ser Glu
        CCACGCGTCCGAGGAAGGAGTCCAGAGACACAGAGAGCAG        ATG AGT TCC GAG
                        10
Thr Gly Pro Val Ala Val Asp Pro Thr Leu Arg Arg Arg Ile Glu
ACA GGC CCT GTA GCT GTT GAT CCC ACT CTG AGG AGA AGA ATT GAG
 20                                          30
Pro His Glu Phe Glu Val Phe Phe Asp Pro Arg Glu Leu Arg Lys
CCC CAC GAG TTT GAA GTC TTC TTT GAC CCC CGG GAA CTT CGG AAA
                          40
Glu Thr Cys Leu Leu Tyr Glu Ile Asn Trp Gly Gly Arg His Ser
GAG ACC TGT CTG CTG TAT GAG ATC AAC TGG GGA GGA AGG CAC AGC
 50                                          60
Ile Trp Arg His Thr Ser Gln Asn Thr Asn Lys His Val Glu Val
ATC TGG CGA CAC ACG AGC CAA AAC ACC AAC AAA CAC GTT GAA GTC
                          70
Asn Phe Ile Glu Lys Phe Thr Thr Glu Arg Tyr Phe Cys Pro Asn
AAT TTC ATA GAA AAA TTT ACT ACA GAA AGA TAC TTT TGT CCA AAC
 80                                          90
Thr Arg Cys Ser Ile Thr Trp Phe Leu Ser Trp Ser Pro Cys Gly
ACC AGA TGC TCC ATT ACC TGG TTC CTG TCC TGG AGT CCC TGT GGG
                         100
Glu Cys Ser Arg Ala Ile Thr Glu Phe Leu Sre Arg Tyr Pro His
GAG TGC TCC AGG GCC ATT ACA GAA TTT TTG AGC CGA TAC CCC CAT
110                                          120
Val Thr Leu Phe Ile Tyr Ile Ala Arg Leu Tyr His His Ala Asp
GTA ACT CTG TTT ATT TAT ATA GCA CGG CTT TAT CAC CAC GCA GAT
                         130
Pro Arg Asn Arg Gln Gly Leu Arg Asp Leu Ile Ser Ser Gly Val
CCT CGA AAT CGG CAA GGA CTC AGG GAC CTT ATT AGC AGC GGT GTT
140                                          150
Thr Ile Gln Ile Met Thr Glu Gln Glu Ser Gly Tyr Cys Trp Arg
ACT ATC CAG ATC ATG ACG GAG CAA GAG TCT GGC TAC TGC TGG AGG
                         160
Asn Phe Val Asn Tyr Ser Pro Ser Asn Glu Ala His Trp Pro Arg
AAT TTT GTC AAC TAC TCC CCT TCG AAT GAA GCT CAT TGG CCA AGG
170                                          180
Tyr Pro His Leu Trp Val Arg Leu Tyr Val Leu Glu Leu Tyr Cys
TAC CCC CAT CTG TGG GTC AGG CTG TAC GTA CTG GAA CTC TAC TGC
                         190
Ile Ile Leu Gly Leu Pro Pro Cys Leu Asn Ile Leu Arg Arg Lys
ATC ATT TTA GGA CTT CCA CCC TGT TTA AAT ATT TTA AGA AGA AAA
```

FIG.1A

```
200                                     210
Gln Pro Gln Leu Thr Phe Phe Thr Ile Ala Leu Gln Ser Cys His
CAA CCT CAA CTC ACG TTT TTC ACG ATT GCT CTT CAA AGC TGC CAT
                    220                                  229
Tyr Gln Arg Leu Pro Pro His Ile Leu Trp Ala Thr Gly Leu Lys
TAC CAA AGG CTA CCA CCC CAC ATC CTG TGG GCC ACA GGG TTG AAA

TGA CTTCTGGGAGTTGGGGATGGATGAAATGACTCCTTGTATGTCTTGACAGCAGCAAT
TGATTACCCACTAAAGAGCGACTGCCACAAGGAATCTAGAAGTCGAAAAAAAAAAAAAAA
AAAAAAAAAAAAAAAAAAAAAAAAAAAAAAAAAA
```

FIG.1B

```
                                          1
                            Met Thr Ser Glu Lys Gly Pro Ser Thr
TGAATTCGTGGGACAGAGCACC      ATG ACT TCT GAG AAA GGT CCT TCA ACC
10                                              20
Gly Asp Pro Thr Leu Arg Arg Arg Ile Glu Pro Trp Glu Phe Asp
GGT GAC CCC ACT CTG AGG AGA AGA ATC GAA CCC TGG GAG TTT GAC
                        30
Val Phe Tyr Asp Pro Arg Glu Leu Arg Lys Glu Ala Cys Leu Leu
GTC TTC TAT GAC CCC AGA GAA CTT CGT AAA GAG GCC TGT CTC CTC
                                            50
Tyr Glu Ile Lys Trp Gly Met Ser Arg Lys Ile Trp Arg Thr Ser
TAC GAA ATC AAG TGG GGC ATG AGC CGG AAG ATC TGG CGA ACG TCA
                    60
                                *
Gly Lys Asn Thr Thr Asn His Val Glu Val Asn Phe Ile Lys Lys
GGC AAA AAC ACC ACC AAT CAC GTG GAA GTT AAT TTT ATA AAA AAA
70                                          80
Phe Thr Ser Glu Arg Asp Phe His Pro Ser Ile Ser Cys Thr Ile
TTT ACG TCA GAA AGA GAT TTT CAC CCA TCC ATC AGC TGC ACC ATC
                                90
                                    *           *
Thr Trp Phe Leu Ser Trp Ser Pro Cys Trp Glu Cys Ser Gln Ala
ACC TGG TTC TTG TTC TTG AGT CCC TGC TGG GAA TGC TCC CAG GCT
100                                         110
Ile Arg Glu Phe Leu Ser Arg His Pro Gly Val Thr Leu Val Ile
ATT AGA GAG TTT CTG AGT CGG CAC CCT GGT GTG ACT CTA GTG ATC
                        120
Tyr Val Ala Arg Leu Phe Trp His Met Asp Gln Gln Asn Arg Gln
TAC GTA GCT CGG CTT TTT TGG CAC ATG GAT CAA CAA AAT CGG CAA
130                                         140
Gly Leu Arg Asp Leu Val Asn Ser Gly Val Thr Ile Gln Ile Met
GGT CTC AGG GAC CTT GTT AAC AGT GGA GTA ACT ATT CAG ATT ATG
                        150
Arg Ala Ser Glu Tyr Tyr His Cys Trp Arg Asn Phe Val Asn Tyr
AGA GCA TCA GAG TAT TAT CAC TGC TGG AGG AAT TTT GTC AAC TAC
160                                         170
Pro Pro Gly Asp Glu Ala His Trp Pro Gln Tyr Pro Pro Leu Trp
CCA CCT GGG GAT GAA GCT CAC TGG CCA CAA TAC CCA CCT CTG TGG
                        180
Met Met Leu Tyr Ala Leu Glu Leu His Cys Ile Ile Leu Ser Leu
ATG ATG TTG TAC GCA CTG GAG CTG CAC TGC ATA ATT CTA AGT CTT
190                                         200
Pro Pro Cys Leu Lys Ile Ser Arg Arg Trp Gln Asn His Leu Thr
CCA CCC TGT TTA AAG ATT TCA AGA AGA TGG CAA AAT CAT CTT ACA
```

FIG.2A

```
                              210
Phe Phe Arg Leu His Leu Gln Asn Cys His Tyr Gln Thr Ile Pro
TTT TTC AGA CTT CAT CTT CAA AAC TGC CAT TAC CAA ACG ATT CCG
220                                     230
Pro His Ile Leu Leu Ala Thr Gly Leu Ile His Pro Ser Val Ala
CCA CAC ATC CTT TTA GCT ACA GGG CTG ATA CAT CCT TCT GTG GCT
    236
Trp Arg OP
TGG AGA TGA ATAGGATGATTCCGTGTGTGTACTGATTCAAGAACAAGCAATGATGAC

CCACTAAAGAGTGAATGCCATTTAGAATCTAGAAATGTTCACAAGGTACCCCAAAACTCT

GTAGCTTAAACCAACAATAAATATGTATTACCTCTGGC
```

FIG.2B

APOLIPOPROTEIN B MRNA EDITING PROTEIN COMPOSITIONS AND METHODS

CROSS-REFERENCE TO RELATED APPLICATION

This application is a continuation-in-part of U.S. patent application Ser. No. 08/015,203, filed Feb. 9, 1993, the disclosure of which is incorporated herein by reference.

TECHNICAL FIELD OF THE INVENTION

The present invention relates to compositions and methods for editing apo B RNA. In particular, the present invention relates to an apo B RNA editing protein as well as to a polynucleotide that encodes that protein and processes for editing apo B RNA and altering apo B protein production.

BACKGROUND OF THE INVENTION

Apolipoprotein B (apo B) is a large hydrophobic protein synthesized in the liver and small intestine of mammals. Apo B serves an essential although incompletely understood role in the assembly and secretion of triglyceride-rich lipoproteins (chylomicrons and very low density lipoproteins) and also functions in the catabolic clearance of low density lipoprotein (LDL), the major transport vehicle of plasma cholesterol of humans.

Mammalian apo B is the product of a single gene which maps to the p23-p24 region of chromosome 2 (Chan, et al. 1985; Mehrabian, et al. 1986; Luo, et al. 1986; Li, et al., 1988). Apo B RNA is expressed and processed in a tissue-specific fashion. One form of apo B is synthesized in the human liver as a protein of 4536 amino acids with a relative molecular mass of about 512,000 daltons. This form of the protein is referred to on a centile scale as apo B100 (Knott, et al. 1986; Yang, et al. 1986; Chen, et al. 1986; Cladaras, et al. 1986; Ludwig, et al. 1987). Several important structural domains have been identified for apo B100 based upon cDNA sequence and monoclonal epitope mapping. The most important of these are the low density lipoprotein (LDL) receptor binding domain and the attachment site of apolipoprotein (a) which both reside in the carboxyl terminal half of the protein (Yang, et al. 1990; Law and Scott 1990; Pease, et al. 1990).

By contrast, the intestinal form of the protein contains about 2152 amino acids, is colinear with the amino terminal half of apo B100, and is referred to as apo B48 (Innerarity, et al. 1987; Hardman, et al. 1987). Apo B48 is found in the systemic circulation in association with intestinally derived lipoprotein particles, namely chylomicrons and chylomicron remnants. Those particles are cleared from the plasma compartment via a principally hepatic receptor that has been partially characterized and is referred to as the low density lipoprotein-receptor related protein or LRP (Herz, et al. 1988; Kowal, et al. 1989). That receptor recognizes apolipoprotein E as its major ligand (Beisegel, et al. 1989).

The biological relevance of apo B48 likely relates to the absence of the apo B100 carboxyl domains. Lipoprotein particles containing apo B48 have a catabolic fate different from those with apo B100 which are cleared principally via the LDL-receptor. The implications for this observation in terms of atherosclerosis susceptibility remain to be tested experimentally but it suggests several models whereby such characteristics of an intestinal particle may have evolved to facilitate their function as an efficient delivery system for dietary triglyceride. By contrast, the finer regulation of plasma cholesterol homeostasis may be achieved through hepatic very low density lipoprotein (VLDL) secretion and ultimately LDL uptake.

The post-transcriptional modification of apo B RNA is referred to as apo B RNA editing. Editing is distinct from other co- or post-transcriptional processing events such as capping, polyadenylation and splicing. Apo B RNA editing represents a departure from one of the central tenets of molecular biology that DNA encodes an RNA template which is identical and which subsequently specifies a predictable protein. Several examples of RNA editing have been described in lower eukaryotes and classified according to the underlying mechanism (Cattaneo 1991; Soliner-Webb 1991) such as post-transcriptional insertion or deletion of uridine residues in trypanosome mitochondrial genes which results in the production of a translationally competent open reading frame. Other forms of RNA editing include the post-transcriptional insertion of guanosine residues in paramyxovirus and cytidine residues in physarum polycephalum.

Apo B RNA editing was described in 1987 when several groups simultaneously reported the site-specific modification of apo B RNA as the underlying mechanism for the production of distinct isoforms of apo B from the human liver and small intestine (Powell, et al. 1987; Chen, et al. 1987; Hospattankar, et al. 1987). Those studies demonstrated that nucleotide 6666 in human and rabbit intestinal apo B cDNA was changed from the genomically templated cytidine to a uridine residue. That change modified codon 2153 from a CAA which encodes glutamine to a UAA which encodes an in-frame stop codon. Those findings indicated that intestinal apo B was likely the product of a single apo B gene in which codon 2153 was altered to produce a translational stop codon and thereby specify a truncated apo B (apo B48) as the primary translation product.

Apo B RNA editing in the mammalian enterocyte occurs as a developmentally regulated event in human (Teng, et al. 1990), rat (Wu, et al. 1990) and pig small intestine (Teng, et al. 1990). Teng et al. demonstrated that human intestinal apo B was more than 90% unedited in fetal small intestinal RNA from late first trimester samples. Teng et al. also demonstrated that the early gestation fetal small intestine synthesizes and secretes both apo B100 and apo B48, indicating that the unedited form of the apo B transcript is translationally competent in the small intestine and, furthermore, leads to apo B100 secretion. As the small intestine undergoes morphological maturation during the second trimester, the proportion of edited apo B RNA increases such that at 19-20 weeks gestation, small intestinal apo B RNA is approximately 80-90% edited. Adult small intestine was found to contain a variable quantity of unedited apo B RNA, varying from 3-19% in one series (Teng et al., 1990).

Rat apo B RNA editing is developmentally regulated in both the small intestine and liver. Wu et al. demonstrated that the temporal sequence of the developmental changes in apo B RNA editing was distinct for the liver and small intestine with a striking increase in intestinal editing prenatally while the hepatic transcript was largely unedited until postnatal day 20. Coleman et at. demonstrated that coordinate changes in rat hepatic triglyceride metabolism occurred over this same time period showing that the emergence of edited apo B RNA in both the rat liver and intestine coincides with developmental changes in triglyceride metabolism (Coleman et al., 1988).

A human colon cancer-derived cell line (Caco-2) which, in culture, undergoes a form of "spontaneous differentiation" and displays certain phenotypic characteristics of developing enterocytes has been used to study apo B RNA editing. During the course of differentiation from pre- to late postconfluency, apo B RNA abundance increased 20-fold but the proportions of edited to unedited transcript remained unaltered at less than 5% at all times studied (Teng et al., 1990). Thus, in this cell line apo B RNA abundance appears to be regulated by mechanisms distinct from those which influence apo B RNA editing. Other investigators (Jiao, et al. 1990) using this cell line have found that apo B RNA editing increases when the cells are grown on semipermeable filters rather than plastic.

Mammalian apo B is expressed in a tissue-specific manner with gene transcription and protein synthesis predominantly confined to the adult liver and small intestine. In the fetus, however, apo B RNA and protein biosynthesis occurs in a number of extraintestinal, extrahepatic sites. In the rat (Wu, et al., 1990; Demmer, et al. 1986) such tissues include the placenta and fetal membranes while in humans, such tissues include lung, kidney, stomach, colon, adrenal and fetal membranes (Teng, et al 1990; Hopkins, et at. 1987). Analysis of PCR amplified cDNA samples indicated that apo B cDNA was edited to a varying extent (10-50%) in all the fetal tissues examined with the notable exception of the liver and in all those tissues, apo B cDNA was edited to a progressively greater extent during development. Those fetal tissues synthesize and secrete apo B100 but not apo B48, thus, demonstrating that apo B mRNA is translationally active in these locations.

Thyroid hormone modulates hepatic apo B RNA editing in the adult rat (Davidson, et al. 1990). Several genes respond to both T3 and high carbohydrate intake (Davidson, et al. 1990). Baum et al. studied groups of rats fasted for 24 to 48 hours and other groups fasted for 48 hours and subsequently fed a high carbohydrate, fat-free diet for 24 or 48 hours (Baum et al., 1990). This maneuver produced a 30-fold range of hepatic triglyceride concentration from a nadir at 48 hours fasting to a peak at 48 hours refeeding a high carbohydrate diet. In association with these changes, apo B synthesis rates were determined following intraportal vein administration of tritiated leucine and quantitative immunoprecipitation of apo B. In animals fasted for 48 hours there was a decrease in the ratio of apo B48 to apo B100 synthesis and a corresponding decrease in hepatic apo B RNA editing. In animals fasted for 48 hours and the refed a high carbohydrate diet for either 24 to 48 hours, there was no apo B100 synthesis detectable and hepatic apo B RNA was greater than 90% edited. In association with these findings, serum apo B isomorphs as demonstrated on Western blots, were found to be altered in parallel such that control animals and animals fasted for 24 to 48 hours demonstrated mostly apo B100 in their serum while animals fasted and refed a high carbohydrate diet demonstrated essentially only apo B48. Apo A-1 and A-IV RNA abundance and protein biosynthesis were also increased approximately 2-4-fold in the animals refed a high carbohydrate diet for 48 hours. Those changes are thus of a lesser magnitude but in the same direction as encountered (Davidson, et al. 1988) with T3 treatment.

Glickman has shown that the administration of ethinyl estradiol to rats for five days produced a decrease in hepatic but not small intestinal apo B RNA editing and a corresponding increase in the relative synthesis rates of apo B100 (Seishima, et al. 1991). Those findings show a strong correlation between hepatic apo B RNA editing and apo B100 synthesis. A decrease in hepatic apo B RNA editing was associated with uncontrolled non-insulin dependent diabetes mellitus (Jiao, et al. 1991).

BRIEF SUMMARY OF THE INVENTION

In one aspect, the present invention provides an isolated protein that edits apo B RNA. Exemplary such proteins have been isolated and purified and found to have an apparent molecular weight of from about 25 to about 28 kilodaltons. A preferred apo B RNA editing protein of the present invention comprises an amino acid residue sequence of about 229 amino acid residues and comprises the amino acid residue sequence of SEQ ID NO: 2. Another preferred apo B RNA editing protein comprises about 236 amino acid residues and comprises the amino acid residue sequence of SEQ ID NO:4.

In another aspect, the present invention provides a polynucleotide that encodes an apo B RNA editing protein. In a preferred embodiment, that polynucleotide is a DNA molecule and, more preferably a cDNA molecule. A polynucleotide of the present invention preferably encodes a protein having the amino acid residue sequence of SEQ ID NO:2 or SEQ ID NO:4.

In an especially preferred embodiment, a polynucleotide of the present invention comprises the DNA sequence of SEQ ID NO:1 from about nucleotide position 42 to about nucleotide position 732, the DNA sequence of SEQ ID NO:1, the DNA sequence of SEQ ID NO:3 from about nucleotide position 23 to about nucleotide position 730, or the DNA sequence of SEQ ID NO:3.

In another aspect, the present invention provides an isolated DNA sequence that encodes an apo B RNA editing protein of the present invention, which DNA sequence when transfected into a cell that contains unedited apo B RNA increases the production of apo B48 in that cell. Preferably, that polynucleotide comprises the nucleotide sequences set forth above.

The present invention further provides an isolated polynucleotide that is complementary to from about 10 to about 50 contiguous nucleotides of SEQ ID NO:1 from about nucleotide position 42 to about nucleotide position 732 or SEQ ID NO:3 from about nucleotide position 23 to about nucleotide position 730.

In another aspect, the present invention provides an expression vector comprising a polynucleotide that encodes an apo B RNA editing protein of the present invention. A preferred expression vector is an adenovirus or a retrovirus vector construct. The present invention further provides a transformed or transfected cell containing a polynucleotide that encodes an apo B RNA editing protein. The present invention further provides a transgenie animal whose somatic cells contain a polynucleotide that encodes an apo B RNA editing protein of the present invention.

In yet another aspect, the present invention provides a pharmaceutical composition comprising an apo B RNA editing protein of this invention, a polynucleotide encoding such a protein or an expression vector comprising such a polynucleotide and a physiologically acceptable carrier.

Still further, the present invention provides a process of preparing an apo B RNA editing protein comprising the steps of:
a) transfecting a cell with an expression vector comprising a polynucleotide that encodes an apo B RNA editing protein to produce a transformed cell; and
b) maintaining the transformed cell under biological conditions sufficient for expression of the protein. Preferably, a polynucleotide used in such a process is the same as set forth above.

In another aspect, the present invention provides a process of editing apo B RNA comprising the steps of:
a) exposing apo B RNA to an apo B RNA editing protein of the present invention; and
b) maintaining the exposed apo B RNA under physiological conditions sufficient for editing of apo B RNA.

In another aspect, the present invention provides a process of altering apo B protein production, which process comprises the steps of:
a) transfecting a cell that contains unedited apo B mRNA with an expression vector comprising a polynucleotide that encodes an apo B RNA editing protein of the present invention; and
b) maintaining that cell under physiological conditions sufficient for apo B protein production. Preferably, a cell is a human liver cell. In a preferred embodiment, altering apo B protein production is decreasing apo B100 protein production or increasing apo B48 protein production.

BRIEF DESCRIPTION OF THE DRAWINGS

In the drawings, which form a portion of the specification:

FIG. 1 shows the DNA sequence (SEQ ID NO:1) and the deduced amino acid sequence (SEQ ID NO:2) of an apo B RNA editing protein (REPR). The nucleotide sequence is 833 bp and contains a poly A-tail of more than 100 bases. This clone has a single open reading frame encoding a 9 amino acid protein with a calculated molecular weight of 27277 Da. REPR contains consensus phosphorylation sites for cAMP-dependent kinase (position 33), protein kinase C (positions 13, 58, 72) and casein kinase (position 145). Two leucine zipper motifs are identified at position 182 to 203 and position 189 to 210.

FIG. 2 shows the DNA sequence (SEQ ID NO:3) and the deduced amino acid sequence (SEQ ID NO:3) of a human apo B RNA editing protein (HEPR). The nucleotide sequence is 879 bp. This clone has a single open reading frame encoding a 236 amino acid protein with a calculated molecular weight of about 27 kD.

DETAILED DESCRIPTION OF THE INVENTION

I. The Invention

Figure 3:
FIG. 3 shows a Western blot of proteins secreted by HepG2 cells transfected with an expression vector containing a coding DNA sequence that encodes an apo B RNA editing protein. Molecular weight markers are indicated on the left. In the figure, C=WT; S=sense and α=αsense. Proteins secreted into the medium were analyzed 48 and 72 hours after transfection.

Mammalian apolipoprotein B (apo B) exists in two forms, each the product of a single gene (Breslow, 1988). The shorter form, apo B48, arises by post-transcriptional RNA editing in which a cytidine deamination produces a UAA termination codon (Powell, et al. 1987; Chen, et al. 1987). Apo B messenger RNA (mRNA) editing is mediated by protein factors that are tissue and species-specific (Hodges, et at. 1992; Driscoll, et al. 1989; Lau, et al. 1990; Smith, et al. 1991; Hodges, et al. 1991; Bostrom, et at. 1990; Driscoll and Casanova 1990; Chen, et al. 1990; Shah, et al. 1991; Garcia, et al. 1991; Teng and Davidson 1992). Full length complementary DNA clones that encode apo B RNA editing proteins have been isolated from rat and human small intestine. Those proteins comprise about 229-236 amino acid residues. The protein isolated from rat (REPR) contains consensus phosphorylation sites and leucine zipper domains.

A. Apo B RNA Editing Protein

In one aspect, the present invention provides an isolated apo B RNA editing protein. An apo B RNA editing protein is necessary for the editing of apo B RNA. As used herein, the term "necessary" means that apo B RNA editing does not occur in the absence of that protein. As set forth hereinafter, however, other factors (including other proteins) are also needed for apo B RNA editing.

A preferred such protein has been isolated and purified from rat small intestine and found to have an apparent molecular weight of about 25 kilodaltons as determined by polyacrylamide gel electrophoresis. That rat apo B RNA editing protein (REPR) comprises an amino acid residue sequence of about 229 amino acid residues, has an apparent molecular weight predicted from that sequence of about 28 kD, and comprises the amino acid residue sequence of SEQ ID NO:2.

Another preferred apo B RNA editing protein has been isolated and purified from human small intestine and found to have an apparent molecular weight of about 27 kD as determined by polyacrylamide gel electrophoresis. That human protein (HEPR) comprises about 236 amino acid residues with a calculated molecular weight of about 28 kD and comprises the amino acid residue sequence of SEQ ID NO:4.

Proteins are disclosed herein as amino acid residue sequences. Those sequences are written left to right in the direction from the amino to the carboxyl terminus. In accordance with standard nomenclature, amino acid residue sequences are denominated by either a single letter or a three letter code as indicated below.

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |

| Amino Acid Residue | 3-Letter Code | 1-Letter Code |
| --- | --- | --- |
| Valine | Val | V |

Modification and changes may be made in the structure of a protein of the present invention and still obtain a molecule having like apo B RNA editing characteristics. For example, certain amino acids can be substituted for other amino acids in a sequence without appreciable loss of editing activity. Because it is the interactive capacity and nature of a protein that defines that protein's biological functional activity, certain amino acid sequence substitutions can be made in a protein sequence (or, of course, its underlying DNA coding sequence) and nevertheless obtain a protein with like properties.

In making such changes, the hydropathic index of amino acids can be considered. The importance of the hydropathic amino acid index in conferring interactive biologic function on a protein is generally understood in the art (Kyte & Doolittle, J. Mol. Biol., 157:105–132, 1982). It is known that certain amino acids can be substituted for other amino acids having a similar hydropathic index or score and still result in a protein with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant protein, which in turn defines the interaction of the protein with other molecules, for example, enzymes, substrates, receptors, antibodies, antigens, and the like. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5 ±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. The present invention thus contemplates functional equivalents of an apo B RNA editing protein as set forth above.

A protein of the present invention is prepared by standard techniques well known to those skilled in the art. Such techniques include, but are not limited to, isolation and purification from tissues known to contain that protein and expression from cloned DNA that encodes such a protein using transformed cells (See the Examples, hereinafter).

B. Polynucleotide Encoding Apo B RNA Editing Protein

In another aspect, the present invention provides a polynucleotide that encodes an apo B RNA editing protein of the present invention. In a preferred embodiment, that polynucleotide is a DNA molecule and, more preferably a cDNA molecule.

As used herein, the term "polynucleotide" means a sequence of nucleotides connected by phosphodiester linkages. A polynucleotide of the present invention can comprise from about 680 to about several hundred thousand base pairs. Preferably, a polynucleotide comprises from about 680 to about 150,000 base pairs. Preferred lengths of particular polynucleotides are set hereinafter.

A polynucleotide of the present invention can be a deoxyribonucleic acid (DNA) molecule or a ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), and uracil (U).

A polynucleotide of the present invention preferably encodes a protein comprising the amino acid residue sequence of SEQ ID NO:2 or SEQ ID NO:4. In an especially preferred embodiment, a polynucleotide of the present invention comprises the DNA sequence of SEQ ID NO:1 from about nucleotide position 42 to about nucleotide position 732, the DNA sequence of SEQ ID NO:1, the DNA sequence of SEQ ID NO:3 from about nucleotide position 23 to about nucleotide position 730 of SEQ ID NO:3, or SEQ ID NO:3.

A polynucleotide of the present invention can be prepared using standard techniques well known to one of skill in the art. The preparation of a cDNA molecule encoding an apo B RNA editing protein of the present invention is described hereinafter in the Examples. A polynucleotide can also be prepared from genomic DNA libraries using lambda phage technologies.

C. Probes and Primers

In another aspect, DNA sequence information provided by the present invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected nucleotide sequence, e.g., a sequence such as that shown in SEQ ID NO:1 or SEQ ID NO:3. The ability of such nucleic acid probes to specifically hybridize to a polynucleotide encoding an apo B RNA editing protein lends them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a gene or polynucleotide that encodes an apo B RNA editing protein from mammalian cells using PCR technology.

To provide certain of the advantages in accordance with the present invention, a preferred nucleic acid sequence employed for hybridization studies or assays includes sequences that are complementary to at least a 10 to 50 or so long nucleotide stretch of a polynucleotide that encodes an apo B RNA editing protein, such as that shown in SEQ ID NO:1 or SEQ ID NO:3. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, 30 to 50 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, herein incorporated by reference, or by excising selected DNA fragments from recombinant plasmids containing appropriate inserts and suitable restriction sites.

Accordingly, a nucleotide sequence of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids. For example, one will select relatively low salt and or high temperature conditions, such as provided by 0.02M–0.15M NaCl at temperatures of 50° C. to 70° C. Those conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate an apo B RNA editing protein coding sequences from other cells, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g., on the G+C contents, type of target nucleic acid, source of nucleic acid, size of hybridization probe). Following washing of the matrix to remove nonspecifically bound probe molecules, specific hybridization is detected, or even quantified, by means of the label.

D. Expression Vector

The present invention contemplates an expression vector comprising a polynucleotide of the present invention. An expression vector of the present invention is an isolated and purified DNA molecule comprising an enhancer-promoter operatively linked to a coding region that encodes an apo B RNA editing protein, which coding region is operatively linked to a transcription-terminating region, whereby the enhancer-promoter drives the transcription of the coding region.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. A preferred such cell is a hepatocyte or liver cell. By employing an enhancer-promoter with well-known properties, the level and pattern of gene product expression can be optimized. For example, selection of an enhancer-promoter that is active specifically in liver cells permits tissue-specific expression of an apo B RNA editing protein. Exemplary and preferred enhancer-promoters are the CMV promoter, the Rous sarcoma virus (RSV) RSV-1 LTR promoter, the fi-actin promoter, the α-antitrypsin promoter, the apo A1 promoter, and the liver fatty acid binding promoter or the albumin promoter.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are re/erred to herein as transcription-termination regions. Those regions are required for efficient polyadenylation of transcribed messenger RNA (RNA). Transcription-terminating regions are well known in the art. A preferred transcription-terminating region used in an adenovirus vector construct of the present invention comprises a polyadenylation signal of SV40 or the protamine gene.

A preferred expression vector is an adenovirus vector construct. The use of adenovirus as a vector for cell transfection is well known in the art. Adenovirus vector-mediated cell transfection has been reported for various cells (Stratford-Perricaudet, et al., 1992).

An adenovirus vector of the present invention is replication defective. A virus is rendered replication defective by deletion of the viral early gene region 1 (E1). An adenovirus lacking an E1 region is competent to replicate only in cells, such as human 293 cells, which express adenovirus early gene region 1 genes from their cellular genome. Thus, such an adenovirus cannot kill cells that do not express that early gene product.

In a preferred embodiment, an adenovirus vector used in the present invention is lacking both the E1 and the E3 early gene regions. Techniques for preparing replication defective adenoviruses are well known in the art (See, e,g. McGrory et al., 1988, and Gluzman et al., 1982).

It is believed that any adenovirus vector can be used in the practice of the present invention. Thus, an adenovirus vector can be of any of the 42 different known serotypes or subgroups A-F. Adenovirus type 5 of subgroup C is the preferred starting material for production of a replication-defective adenovirus vector.

An adenovirus is engineered to contain a coding DNA sequence for use as a vector. Individual DNA sequences such as cDNAs that encode a gene product are inserted into the adenovirus to create a vector construct. In a preferred embodiment, a coding sequence for an apo B RNA editing protein is introduced or incorporated into an adenovirus at the position from which the E1 coding sequences have been removed. However, the position of insertion within the adenovirus sequences is not critical to the present invention. A coding sequence can also be inserted in lieu of the deleted E3 region in E3 replacement vectors as described previously by Karlsson et al. (1986). Preferably, the E1 region of adenovirus is replaced by the coding DNA sequence or gene.

The resulting adenovirus vector is co-transfected into 293 cells together with a plasmid carrying a complete adenovirus genome to propagate the adenovirus. An exemplary such plasmid is pJM17. Co-transfection is preformed in accordance with standard procedures well known in the art. By way of example, 293 cells are cultured in Dulbecco's modified Eagle's medium containing fetal calf serum. Confluent cultures are split the day before calcium phosphate cotransfection of plasmids. After addition of the DNA to the cells, the cells are shocked (e.g., a 15% glycerol shock) to boost transfection efficiency and the cells are overlaid with agar in DMEM containing fetal calf serum, penicillin, streptomycin sulfate, and other antibiotics or antifungal agents as needed. Monolayers are incubated until viral plaques appear (about 5–15 days).

Those plaques are picked, suspended in medium containing fetal calf serum, and used to infect a new monolayer of 293 cells. When greater than 90% of the cells showed infection, viral lysates are subjected to a freeze/thaw cycle and designated as primary stocks. The presence of recombinant virus is verified by preparation of viral DNA from infected 293 cells, restriction analysis, and Southern blotting. Secondary stocks are subsequently generated by infecting 293 cells with primary virus stock at a multiplicity of infection of 0.01 and incubation until lysis.

The particular cell line used to propagate the recombinant adenoviruses of the present invention is not critical to the present invention. Recombinant adenovirus vectors can be propagated on, e.g., human 293 cells, or in other cell lines that are permissive for conditional replication-defective adenovirus infection, e.g., those which express adenovirus E1 gene products "in trans" so as to complement the defect in a conditional replication-defective vector. Further, the cells can be propagated either on plastic dishes or in suspension culture, in order to obtain virus stocks thereof.

Other viruses can also be used as expression vectors. Exemplary such viruses are HSV-2, picornavirus, coronovirus, eunyavirus, togavirus, rahbdovirus, retrovirus, vaccinia virus and parvovirus (See. e.g. Walsh et al., 1992; Sutter et al., 1992; Huber et al., 1991; Hatzoglou et al., 1990; Zwiebel et al., 1989). As discussed with regard to adenoviruses, those viruses would also be altered in such a way as to render them non-pathogenic.

By way of example, a polynucleotide of the present invention can be incorporated into a parvovirus such as the human parvovirus, the adeno-associated virus. Means for incorporating DNA sequences into such a parvovirus are well known in the art (Walsh et al., 1992).

E. Transformed Cell

In another aspect, the present invention provides a cell transformed or transfected with one or more polynucleotides of the present invention as well as transgenic cells derived from those transformed or transfected cells. Means of transforming or transfecting cells with exogenous polynucleotides such as DNA molecules are well known in the art and include techniques such as calcium-phosphate- or DEAE-dextran-mediated transfection, protoplast fusion, electroporation, liposomes, direct microinjection and adenovirus infection (Sambrook, Fritsch and Maniatis, 1989).

The most widely used method is transfection mediated by either calcium phosphate or DEAE-dextran. Although the mechanism remains obscure, it is believed that the transfected DNA enters the cytoplasm of the cell by endocytosis and is transferred to the nucleus. Depending on the cell type, up to 20% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that carry integrated copies of the foreign DNA, which are usually arranged in head-to-tail tandem arrays.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transferred to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. In addition, DNA that is coated with a synthetic cationic lipid can be introduced into cells by fusion.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

The use of adenovirus as a vector for cell transfection is well known in the art. Adenovirus vector-mediated cell transfection has been reported for various cells (Stratford-Perricaudet, et al., 1992).

F. Transgenic Mammal

In another aspect, the present invention provides a transgenic mammal having incorporated into its genome a selected transgene that encodes a polypeptide that edits apo B RNA. In a preferred embodiment, the polypeptide comprises the amino acid residue sequence of SEQ ID NO:2 or SEQ ID NO:4.

As used herein, the term "transgene" is intended to refer broadly to the introduction of any desired DNA sequence into the animal's genome, including but not limited to, genes or DNA sequences which are perhaps not normally present in the genome, genes which normally both are present but not normally transcribed and translated ("expressed") in a given genome, additional copies of genes which are present and expressed in a given genome, or any other genes or DNA sequences which one desires to introduce into the genome. This can include genes which may normally be present in the non-transgenic genome but which one desires to have altered in expression, or which one desires to introduce in an altered or variant form.

The term "genome" is intended to include the entire DNA complement of an organism, including the nuclear DNA component, chromosomal or extrachromosomal DNA, as well as the cytoplasmic domain (e.g., mitochondrial DNA). Thus, the present invention contemplates that one or more transgenes can be stably incorporated into an organism's germ cells or somatic cells, in a functional form, and achieve a desired effect, such as conferring a selected trait to the transgenic animal.

As used herein, the phrase "incorporated into their genome" is intended to refer to mice or other mammals which have a selected transgene introduced into their germ cells and/or somatic cells such that it is stably incorporated and is capable of carrying out a desired function.

Introduction of the DNA into the germ cells is most conveniently achieved by a technique known as microinjection, wherein a solution containing DNA is introduced through the aid of a microscope and a microinjector pipet which deposits intact DNA into one of the two pronuclei. However, the invention contemplates that other techniques may be employed for introduction of the DNA into the genome, including in vitro fertilization using sperm as a carrier of exogenomic DNA, or electroporation or transfection into an embryonic stem cell line and introduction of these cells into an animal blastocyst (See, e.g., PCT Publication No. WO 90/03432; Mansour, 1990; Frohman et al., 1989).

A preferred method for preparing a transgenic mammal includes subjecting a female to hormonal conditions effective to promote superovulation, followed by fertilizing eggs produced by the superovulated female, and introducing the selected transgene into the fertilized eggs. In this embodiment, the fertilized eggs having the selected transgene is transferred into a pseudopregnant or receptive female, and the embryo is brought to term. While the presently preferred method of fertilization is in vitro fertilization, superovulated eggs could be fertilized by artificial insemination of the female or by breeding the female with a fertile male. As noted, the selected transgene is introduced into the fertilized eggs by any one of several convenient methods, for example, by microinjection, and it is also possible to introduce the DNA prior to fertilization. Transferral of fertilized eggs having the selected transgene into a pseudo pregnant or receptive female can be accomplished using techniques well-known in the art (U.S. Pat. No. 4,736,866).

Transgenic mammals can also be prepared using retroviral expression vectors (PCT Publication No. WO 90/08832). Briefly, a retroviral vector is introduced intracellularly into an appropriate embryo. In a preferred embodiment, a retroviral vector is microinjected into the subzonal (perivitelline) space. Preferably, the zona pellucida remains intact.

G. Pharmaceutical Composition

In yet another aspect, the present invention provides a pharmaceutical composition comprising (1) an apo B RNA editing protein of the present invention, a polynucleotide encoding such a protein or an expression vector comprising such a polynucleotide and (2) a physiologically acceptable carrier.

A composition of the present invention is typically administered parenterally in dosage unit formulations containing standard, well known nontoxic physiologically acceptable carriers, adjuvants, and vehicles as desired. The term parenteral as used herein includes intravenous, intramuscular, intraarterial injection, or infusion techniques.

Injectable preparations, for example, sterile injectable aqueous or oleaginous suspensions are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminant, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifigation.

A carrier can also be a liposome. Means for using liposomes as delivery vehicles are well known in the art (See, e.g., Gabizon et al., 1990; Ferruti et al., 1986; and Ranade, V. V., 1989).

A transfected cell can also serve as a carrier. By way of example, a liver cell can be removed from an organism, transfected with a polynucleotide of the present invention using methods set forth above and then the transfected cell returned to the organism (e.g. injected intravascularly).

H. A Process of Preparing an Apo B RNA Editing Protein

Still further, the present invention provides a process of preparing an apo B RNA editing protein comprising the steps of:
a) transfecting a cell with an expression vector comprising a polynucleotide that encodes an apo B RNA editing protein to produce a transformed cell; and
b) maintaining the transformed cell under biological conditions sufficient for expression of the protein.

Means for transfecting a cell are the same as set forth above. Preferably, a polynucleotide is contained in an expression vector as set forth above. A preferred polynucleotide for use in such a process encodes the amino acid residue sequence of SEQ ID NO:2 or SEQ ID NO:4. More preferably, a polynucleotide comprises the nucleotide sequence of SEQ ID NO:1 from about nucleotide position 42 to about nucleotide position 732, the nucleotide sequence of SEQ ID NO:1, the nucleotide sequence of SEQ ID NO:3 from about position 23 to about position 730, or the nucleotide sequence of SEQ ID NO:3.

Biological conditions include temperature, pH, osmolality and the like as is well known in the art. In a preferred embodiment, temperature is from about 20° C. to about 50° C., more preferably from about 30° C. to about 40° C. and, even more preferably about 37° C.

pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/1 and, more preferably from about 290 mosm/L to about 310 mosm/L. Other biological conditions needed for transfection and expression of an encoded protein are well known in the art.

I. Process of Editing Apo B RNA

The present invention contemplates a process of editing apo B RNA. In accordance with such a process, apo B RNA is exposed to an effective editing amount of an apo B RNA editing protein of this invention. The exposed apo B RNA is then maintained under physiological conditions sufficient for apo B RNA editing. The apo B RNA to be edited is provided in a liquid medium that contains other factors necessary for editing.

Thus, a process of editing apo B RNA comprises the steps of:
a) exposing apo B RNA to an apo B RNA editing protein; and
b) maintaining the exposed apo B RNA under physiological conditions sufficient for editing of apo B RNA.

Any apo B RNA can be used in an editing process so long as the nucleotide sequence of that RNA contains a target sequence recognized and edited by an apo B RNA editing protein. Thus, apo B RNA can be messenger RNA (mRNA) or synthetic RNA such as cRNA.

Although not wishing to be bound by any particular theory, it is believed that apo B RNA editing most likely involves a site-specific deamination of the cytosine at nucleotide 6666 of apo B RNA. The nucleotide sequence spanning that edited base at position 6666 is highly conserved in mammalian apo B cDNA's.

The minimal length of apo B RNA sequence information needed for editing varies according to the source of such RNA and whether editing occurs in vitro, in situ or in vivo. Davies, et al. determined that a 26 nucleotide region of human apo B RNA flanking the edited base was as efficiently edited as the endogenous (rat) transcript when transfected into McA7777 cells. On the other hand, Caco-2 cells edit a 354 and 186 base pair, but not a 63 base pair chimeric construct following stable transfection (Bostrom, et al. 1989; Bostrom, et al. 1990). A human apo B RNA sequence of 26 nucleotides can be edited in vitro using S100 extracts prepared from rat enterocytes. Thus, it is likely that there are true biological differences in editing activity within different cell types which may, additionally, be more or less preserved during the preparation of S100 extracts.

There is also some nucleotide specificity for apo B RNA editing. Chen, et al. used a coupled transcription editing reaction to demonstrate that in a series of mutations in a 9-nucleotide sequence flanking the edited base, in only 2 of 22 such mutants (a transversion mutant changing the wild type ATACAATTT to ATT CTATTT and a deletion mutant ATAC-TTTT) was editing abolished. (Chen et al. 1990) In that study, however, there was only a low level (less than 2% of the input apo B RNA) of editing by rat liver nuclear extracts. Shah (Shah, et al. 1991) systematically mutagenized a 55 base pair region of human apo B cDNA and demonstrated that the minimal sequence information required for in vitro editing by rat enterocyte S100 extracts is contained within a 26 nucleotide stretch flanking the edited base. However, those workers found an 11 nucleotide region downstream of position 6666 in which all but one point mutations abolished editing.

Yao et al. transfected McA-RH7777 cells with mutated forms of apo B RNA and examined the production of apo B48 in those transfected cells. Where codon 2153 of apo B RNA (CAA) was changed to GAT (eliminating the 'C' at position 6666) apo B48 production was unchanged. Production of a truncated apo B protein was also unchanged where codon 2153 was unaltered but the four or five codons 5' or 3' to that codon were mutated. Apo B48 production was inhibited where the mutated apo B RNA contained a CTA at codon position 2153 (a leu-leu mutation)(leaving the 'C' at position 6666 unchanged, but preventing the formation of a stop codon after editing even if the 'C' is changed to a 'U' upon editing). Recent studies (Davidson and Yao, unpublished) indicate that transfection of a nearly full-length human apo B cDNA containing the leu-leu mutation results in production of a truncated apo B protein.

There may also be some species specificity to apo B RNA editing. Transgenic mice expressing full length human apo B100 mRNA did not significantly edit that human apo B mRNA despite normal editing of endogenous mouse apo B mRNA (Xiong et al., 1992).

The present inventors have recently demonstrated that chick apo B RNA is not edited in-vivo by small intestinal enterocytes and that the chick apo B cDNA sequence is divergent from mammalian apo B cDNA's with 3 changes from the conserved mammalian sequence noted in the 11 nucleotide cassette described by Shah (Shah, et al. 1991; Teng, et al. 1991). These changes would be predicted to abolish in-vitro apo B RNA editing according to the data of Shah. No editing could be detected when chick apo B RNA was incubated in vitro with S100 extracts prepared from rat enterocytes while human, rat and porcine apo B RNA's were all efficiently edited. Further, a second edited base has been identified in human apo B RNA at position 6802 which changes threonine (ACA) to isoleucine (AUA) at codon 2198 (Navaratnam, et al., 1991). Such editing is of no functional consequence because the transcript is terminated upstream of this nucleotide in all instances examined. Because of the sequence homology flanking both edited sites, such data reinforces the hypothesis that the requisite information for editing is contained within the 26 nucleotides flanking position 6666.

One source of RNA that can be used in an editing process of the present invention is synthetic RNA made to contain the edited base. One means of preparing such synthetic RNA has been previously described (Teng et al., 1992).

By way of example, plasmid pGEM-CAA, containing a human genomic apo B fragment (nucleotides 6506–7835), is constructed and transcribed in vitro using T7 RNA polymerase, producing a 221 bp synthetic RNA (nucleotides 6506–6727). pRBF-CAA is constructed using a 470-bp fragment of rat apo B100 cDNA (nucleotides 6512–6982) and cloned into the Sma I site of pGEM4Z (Promega). pRBF-CAA is linearized at a Bam HI site and transcribed with SP6 RNA polymerase producing a 364-bp synthetic RNA.

Plasmid pRB3-CAA is constructed using a 234-bp of rat apo B100 cDNA (nucleotides 6512–6756) and cloned into the EcoRI/HindIII sites of pGEM3Zf(+) (Promega). pRB3-CAA is linearized at a HindIII site and transcribed using T7 RNA polymerase producing a 234 bp synthetic RNA. pCB-CAA is constructed using a 343-bp fragment of chicken apo B CDNA (nucleotides 6604–6860) and cloned into the EcoRI/HindIII site of pGEM3Zf(+) (Promega). pCB-CAA is linearized with Ssp I and transcribed with T7 RNA polymerase producing a 336-bp synthetic RNA. Linearized plasmid DNA (1 µg) is transcribed at 37° C. for 60 minutes in 40 mM Tris-HDI (pH 8.0), 0.25 mM NaCl, 8 mM MgCl$_2$, 2 mM spermidine, 5 mM dithiothreitol (DTT), 750 µM each ATP, CTP, GTP, and UTP, and 20 units of T7 or SP6 RNA polymerase (Promega). The reaction products are treated with RNase-free DNase 1 (Boehringer Mannheim), extracted with phenol-chloroform and purified through Qiagen tip-5 columns as described (Qiagen, Studio City, Calif.).

Apo B RNA can be edited in vitro, in situ or in vivo. Driscoll, et al. described an in vitro system to examine apo B RNA editing using cytoplasmic S100 supernatants prepared from McA7777 cells, a rat hepatoma line which synthesizes and secretes both apo B100 and apo B48 and which, therefore, provides a ready source of "editing activity" to examine possible in vitro RNA modification.

In accordance with such an in vitro system, McA7777 cell extracts are incubated with various lengths of synthetic apo B RNA prepared from the region flanking the edited base. To detect the edited single nucleotide change, an antisense apo B oligonucleotide (35-mer) is annealed downstream from the edited base at position 6666 and extended with reverse transcriptase in the presence of dATP, dCTP, dTTP and dideoxy-GTP as a chain terminator. There being no other "C" residues between the 5' end of the antisense oligonucleotide and the edited base, the primer is extended until it reaches the first upstream "C". If nucleotide 6666 is unedited, the primer undergoes chain termination and produces an extension product of 42 base pairs. If nucleotide 6666 is edited to a "U" then the primer extends to the next upstream "C", at 6655 in human apo B cDNA and 6661 in rat and mouse apo B CDNA. The extended and terminated primers are resolved effectively by urea-acrylamide electrophoresis.

Relatively low levels of in vitro apo B RNA editing can be observed with McA7777 cells or other cellular or nuclear extracts from liver cells. Studies from a number of labs indicate that the yield and functional activity of small intestinal S100 extracts is considerably higher than that reported for the rat liver. Using isolated rabbit, (Bostrom, et al. 1990) rat (Greeve, et al. 1991) or baboon (Driscoll et al. 1990) enterocyte S100 extracts, in vitro conversion rates of from about 10 percent to about 40 percent of input RNA have been reported. Greeve, et al. have detailed extensive findings in regard to the characterization of rat enterocyte S100 editing activity.

A functional complementation assay for apo B RNA editing has been developed based upon the recent observation that chicken apo B RNA is not edited but chicken enterocyte S100 extracts enhance in vitro editing of mammalian apo B RNA (Teng and Davidson, 1992). Poly (A)+intestinal RNA was size fractionated (Sumikawa et at. 1984) and injected into Xenopus oocytes. One fraction yielded editing activity in oocyte extracts, a function dependent upon the addition of chicken enterocyte S100 extract. This functionally active RNA fraction was used to construct a plasmid cDNA library which contained approximately $1 \times 10^6$ cDNA clones.

Screening was carried out using sib selection which led to the isolation of a single positive clone designated apo B RNA editing protein, REPR. In the presence of chicken enterocyte S100 extracts, oocyte homogenates expressing this protein edit more than 50% of a synthetic rat apo B RNA in vitro (See Example 3, hereinafter).

Certain other factors are needed for apo B RNA editing. By way of example, oocyte extracts expressing REPR edit apo B RNA only in the presence of either chicken or rat intestinal S100 extract. The leucine zipper domains in REPR have been postulated to stabilize the interaction of heterodimeric and monodimeric protein complexes (Landschultz et al. 1988). When linearized at a convenient Sty I site (FIG. 1), located at nucleotide 543, upstream of the leucine zipper domains, the in vitro translated protein had an apparent molecular mass of 20 kDa as compared to 25 kDA for the full length translation product. Elimination of the leucine zipper domains from REPR completely abolished its editing activity in oocyte extracts suggesting a critical role for this region of the protein.

The interaction of REPR with other sources of cytoplasmic S100 extract was investigated as a means of providing insight into the cell-specific distribution of the apo B RNA editing machinery. G-292 cells have been previously shown to edit transfected apo B RNA although they, like CHO cells, do not express endogenous apo B RNA (Bostrum, et al. 1990). S100 extracts were also prepared from HepG2 cells, where apo B RNA is present but unedited and McA7777 cells where apo B RNA is present and edited at a low level. No editing activity was detectable with these S100 extracts either alone or together with chicken enterocyte S100 extracts. The addition of REPR to the S100 extracts showed the HepG2 and MCA7777 edited 23% and 30% respectively of rat apo B RNA in vitro, while G292 and CHO cell extracts failed to complement REPR activity.

Physiological conditions sufficient for apo B RNA editing include temperature, pH, osmolality and the like. Means for selecting such conditions for RNA editing are well known in the art. Particular conditions used will vary depending upon whether editing is occurring in vitro, in situ, or in vivo. Where editing occurs in situ in an isolated cell or in vivo, physiological conditions are those necessary to sustain viability of the cell or organism. Thus, temperature is about 35° C. to about 40° C., pH is about 6.8 to about 7.8 and osmolality is about 200 milliosmols/liter (mOsm) to 400 mOsm.

Where editing is in vitro, temperature is preferably from about 4° C. to about 50° C., more preferably from about 20° C. to about 40° and, even more preferably about 30° C. pH is preferably from about a value of 6.0 to a value of about 8.5, more preferably from about a value of 7.5 to a value of about 8.0 and, even more preferably, about a value of 8.0. Osmolality can range from a value of about 100 mOsm to a value of about 400 mOsm and, preferably from a value of about 200 mOsm to a value of about 300 mOSm. Other substances such as buffers, chelators reducing agents and the like can be present as needed (See Example 3 hereinafter).

J. Process of Altering Apo B Protein Production

Because the production of the various forms of apo B depends upon the population of RNA for those forms, a change in apo B RNA editing activity is associated with a change in apo B protein production. Thus, an increase in apo B RNA editing activity increases the production of apo B48, decreases the production of apo B100 or both.

In another aspect, therefore, the present invention provides a process of altering apo B protein production. Such a process comprises the steps of:
 a) transfecting a cell that contains unedited apo B mRNA that encodes apo B100 protein with an expression vector comprising a polynucleotide that encodes an apo B RNA editing protein; and
 b) maintaining that cell under physiological conditions sufficient for apo B protein.

Preferably, a cell is a liver cell and, more preferably a human liver cell such as an HepG2 cell. In a preferred embodiment, altering is increasing the production of apo B48 or decreasing the production of apo B100. In an especially preferred embodiment, altering apo B protein production is increasing the production of apo B48 and decreasing the production of apo B100.

A preferred expression vector is the same as set forth above. Physiological conditions are also preferably the same as set forth above. A detailed description of HepG2 transfection with an expression vector comprising a polynucleotide that encodes an apo B RNA editing protein of the present invention and the effects of that transfection on apo B protein production is set forth hereinafter in the Examples.

The present invention also contemplates an isolated DNA sequence that encodes an apo B RNA editing protein, which DNA sequence when transfected into a cell containing unedited apo B mRNA, alters apo B protein production.

The ability of a process of the present invention to alter apo B RNA editing depends inter alia to some extent on the site specific incorporation of a polynucleotide of this invention into the genome of a target cell.

Such site specific incorporation is known in the art as homologous recombination. As is well known in the art, homologous recombination is particularly useful where inhibition of endogenous gene transcription and translation is desired. By way of example, where apo B RNA editing is active in a cell, such editing can be inhibited by inserting into that cell's genome at the site of the apo B RNA editing protein gene an exogenous DNA segment that does not encode an apo B RNA editing protein. A preferred method for homologous recombination using embryonic stem cells has been described by Mansour (Mansour, 1990).

A process of altering apo B protein editing can be accomplished in vitro or in vivo. Where altering occurs in vivo, a polynucleotide that encodes an apo B RNA editing protein is delivered to a target cell to be transfected. Delivering is preferably administering the polynucleotide into the circulatory system of the subject. In a more preferred embodiment, administering comprises the steps of:

(a) providing a vehicle that contains the polynucleotide; and (b) administering the vehicle to the subject.

A vehicle is preferably a cell transformed or transfected with the polynucleotide or a transfected cell derived from such a transformed or transfected cell. An exemplary and preferred transformed or transfected cell is a leukocyte such as a tumor infiltrating lymphocyte or a T cell or an embryonic stem cell. Means for transforming or transfecting a cell with a polynucleotide of the present invention are set forth above.

Alternatively, the vehicle is a virus or an antibody that specifically infects or immunoreacts with an antigen of the tumor. Retroviruses used to deliver the constructs to the host target tissues generally are viruses in which the 3'LTR (linear transfer region) has been inactivated. That is, these are enhancerless 3'LTR's, often referred to as SIV (self-inactivating viruses) because alter productive infection into the host cell, the 3'LTR is transferred to the 5' end and both viral LTR's are inactive with respect to transcriptional activity. A use of these viruses well known to those skilled in the art is to clone genes for which the regulatory elements of the cloned gene are inserted in the space between the two LTR's. An advantage of a viral infection system is that it allows for a very high level of infection into the appropriate recipient cell.

K. Process of Screening for Apo B RNA Editing Factors

As set forth above, the editing of apo B RNA requires factors other than the apo B RNA editing protein of the present invention. An apo B RNA editing protein of the present invention can be used in an assay process for identifying other factors necessary for editing. In accordance with such a process, a sample of unedited apo B RNA is provided in a liquid medium that contains an apo B RNA editing protein of the present invention. A sample suspected of containing an apo B RNA editing factor is admixed with the liquid medium and the admixture is maintained under physiological conditions for a period of time sufficient for apo B RNA editing to occur. The apo B RNA is then recovered from the admixture and analyzed for editing.

The following Examples illustrate particular embodiments of the present invention and are not limiting of the claims and specification in any way.

EXAMPLE 1

Expression cloning of rat apo B RNA editing protein.

About 100 μg of poly (A)+intestinal RNA was fractionated by sucrose-gradient ultracentrifugation (Sumikawa, et al. 1984). Xenopus oocytes injected with $H_2O$ or 100 ng of size-fractionated intestinal poly (A)+RNA demonstrated a single fraction (number 4) with in vitro editing activity in the presence of chicken intestinal S100 extract. A single fraction, fraction 4, was used to prepare a eDNA library using the Superscript Plasmid System (BRL). Plasmid DNA was linearized with Not I and used for in vitro transcription and capping. RNA was dissolved in $H_2O$ (1 μg/μl) and injected into Xenopus oocytes as described (Kayano, et al. 1990). Oocytes were incubated at 19° C. for 48 hours, homogenized in Dignam buffer A containing protease inhibitors (Teng, et al. 1992) and dialyzed for 2-8 hours against Dignam buffer D (Dignam, et al. 1983). Protein concentration was determined colorimetrically (Bradford 1976) and the homogenate stored at −80° C.

The homogenate was subsequently functionally screened with sib selection (McCormick 1987) to identify a single positive clone, number 131. 100 ng of synthetic RNA transcribed from this clone produced over 50% editing of synthetic rat apo B RNA when assayed in the presence of chicken intestinal S100 extract.

EXAMPLE 2

Nucleotide sequence of cDNA encoding the apo B RNA editing protein (REPR) and deduced amino-acid sequence.

Clone 131 isolated from the library using oocyte expression system as set forth in Example 1 was completely sequenced on both strands using the Sequenase (USB) and dsDNA Cycle Sequencing System (BRL). Internal oligonucleotides were synthesized on an Applied Biosystems 430A synthesizer and used as primers for sequencing. The DNA sequence is shown in FIG. 1 and SEQ ID NO: 1.

The nucleotide sequence comprises about 833 base pairs and contains a poly A-tail of more than about 100 bases. The nucleotide sequence has a single open reading frame that encodes a protein of 229 amino acid residues.

Northern Blots were prepared using 20 μg of total RNA from the following adult rat tissues; Brain (B); heart (H); lung (L); stomach (St); liver (Li); spleen (Sp); kidney (K); colon (C); small intestine (SI); and testis (T).

5 μg of poly(A)+RNA of liver and small intestine were fractionated through 1% agarose, 6% formaldehyde gel prior to capillary transfer and high stringency hybridization (Teng and Davidson, 1992). Northern blots were hybridized with a 422 bp SmaI-KpnI fragment of clone 13 1 which was labelled by random priming. The autoradiogram was exposed at −80° C. with two intensifying screens for six days.

A 1.0 kb transcript is present at highest abundance in small intestine and at lower levels in colon while a 1.24 kb transcript is found at high levels in liver with lower levels in kidney, spleen and lung. No signal was found in brain heart, stomach, or testis. The size of the clone is compatible with the RNA species identified by Northern analysis and indicates a likely full length clone.

The amino-acid sequence was deduced from a codon preference plot (DNA-star). That sequence is shown in FIG. 1 and in SEQ ID NO: 2. Two leucine zipper domains were identified as spanning residues 182-210. A first such domain spans residues 183 to 203 and a second such domain spans residues 189 to 210.

The amino acid residue sequence of SEQ ID NO: 2 also contains consensus phosphorylation sites for cAMP-dependent kinase (residue 33), protein kinase C (residue 13, 58, 72) and casein kinase (residue 145).

EXAMPLE 3

Apo B RNA Editing Activity with REPR

The editing activity of the apo B RNA editing protein prepared in accordance with the procedures of Examples 1 and 2 was studied in an in vitro RNA conversion assay using S100 extracts prepared from rat or chicken enterocytes as previously described (Teng, et al. 1992).

Briefly, each assay contained about 0.8–2.0 ng (2–20 fmol) of synthetic apo B100 RNA prepared as described above, S-100 extract [10 μg chick enterocyte S100 extract (+), 10 μg rat enterocyte S100(+) or 10 μg oocyte homogenate (+)], 200 ng of tRNA, 10 mM Hepes, pH 7.9, 100 mM KCl, 0.25 mM EDTA, 0.25 mM DTT, and 30 units of RNA-guard (Pharmacia) in a final volume of 20 μl (18). After incubation at 30° C. for about 2–3 h, RNA was reisolated and analyzed by primer extension using dideoxy-GTP. In control experiments RNA was incubated with Dignam buffer only. Primer extension assays for human and porcine apo B RNA used primer BT1, giving products of 43 nucleotides for unedited apo B RNA (CAA), 53 nucleotides for edited human apo B RNA and porcine apo B RNA. Rat apo B RNA primer extension analysis used primer BT5, giving products of 43 nucleotides (CAA) and 48 nucleotides (UAA). Chicken apo B RNA primer extension analysis was performed with primer BT11, giving products of 31 nucleotides (CAA) and (theoretically) 37 nucleotides (UAA). The products were fractionated on an 8% polyacrylamide-urea gel and analyzed by scanning laser densitometry of the autoradiograph.

Following in vitro incubation, synthetic apo B100 RNA was subjected to cDNA synthesis and amplification by PCR using apo B-specific oligonucleotides; for rat apo B cDNA, ND1 and ND3, and for chicken, oligonucleotides C7 and C8. DNA was initially denatured at 95° C. for 5 minutes, followed by 25 cycles of denaturation at 92° C. for 1 minutes, annealing at 55° C. for 30 s, and extension at 72° C. for 1.5 minutes with a final 10-minutes extension of 72° C. PCR products were cloned into the Sma I site of pGEM3Zf(+) and sequenced as described above.

The preparation of enterocyte S100 extracts was carried out as previously described (Driscoll, et al. 1989). Briefly, enterocytes from adult, male Sprague-Dawley rats and 10–15-day-old White Leghorn chickens were isolated using citrate-EDTA chelation as described with the exception that a single 30-minutes incubation in solution B was used. Intestinal cells were washed twice with cold phosphate-buffered saline and cytosolic S-100 extracts subsequently prepared according to the method of Dignam. Cells were suspended in 5 volumes of Dignam buffer A (10 mM Hepes, pH 7.9, 1.5 mM MgCl$_2$, 10 mM KCl, 0.5 mM DTT) containing protease inhibitors (10 μg/ml leupeptin, 10 μg/ml antipain, 1 mM benzamidine, and 0.5 mM phenylmethysulfonyl fluoride (PMSF).

Cells were homogenized in a Dounce homogenizer with a type B pestle. After centrifugation for 10 minutes at 2000 rpm in a Sorvall RT6000 centrifuge, the supernatant was adjusted by adding 0.11 volumes of Dignam buffer B (300 mM Hepes, pH 7.9, 1.4M KCl, and 30 mM MgCl$_2$). The homogenate was centrifuged for 1 h at 100,000×g and the supernatant dialyzed for 8 h against buffer D (20 mM Hepes, pH 7.9, 25% glycerol, 100 mM KCl, 0.5 mM EDTA, 0.5 mM DTT, 0.5 mM PMSF). Protein concentration was determined colorimetrically and the final cytosolic S-100 extract was stored in aliquot at −80° C.

RNA encoding REPR was transcribed from a cDNA template and injected into xenopus oocytes. After 48 hours at about 19° C., the oocytes were homogenized in Dignam buffer A containing protease inhibitors, briefly centrifuged and the supernatant dialyzed against Digham buffer D. This material was then used in subsequent apo B RNA conversion assays as set forth above.

The data show that apo B RNA is edited in the presence of oocyte homogenate containing apo B RNA editing protein. The editing activity of that protein was evident only when apo B RNA was incubated in the presence of S100 extract co-factors.

Additional studies were performed using S100 extracts from a variety of cells. S100 extracts were prepared from G292, HepG2, CHO, and MCA7777 cells and assayed alone (no addition) or with 10 μg chick enterocyte S100 extracts (+chick S100). No in vitro editing was observed with either condition. In the presence of 10 μg oocyte homogenate (expressing apo B RNA editing protein)(+oocyte homogenate), a significant level of in vitro editing was observed with both HepG2 and McA7777 extracts.

EXAMPLE 4

Role of the Leucine Zipper Domains in REPR

Apo B RNA editing was studied in vitro using either a full length apo B RNA editing protein (See example 1) linearized with Not I or a truncated apo B RNA editing protein lacking the leucine zipper domains of residues 183–210. The truncated protein was prepared by linearizing the protein of SEQ ID NO: 2 with Sty I.

Approximately 1 μg of capped synthetic RNA was transcribed and translated with $^{35}$S-methionine using an in-vitro translation kit (BRL). The products were isolated and analyzed using denaturing sodium dodecylsulphate −12.5% acrylamide gel electrophoresis and Coomassie blue staining.

The results show that the Sty I truncated protein did not edit apo B RNA.

EXAMPLE 5

In Vivo Editing

An expression vector was constructed by incorporating a DNA sequence that encodes REPR apo B RNA editing protein into plasmid pCMV-4. The encoding sequence is under the control of a CMV enhancer-promoter and is operatively linked to an SV-40 polyadenylated transcription-terminating region. HepG2 cells were transfected with that vector using calcium-phosphate precipitation and maintained under physiological conditions in culture medium from about 48 to about 72 hours.

Aliquots of culture medium containing proteins secreted from the transfected cells were analyzed 48 and 72 hours after transfection using a Western Blot. The results are shown in FIG. 3.

The data in FIG. 3 show that HepG2 cells transfected with an expression vector containing a coding sequence for REPR apo B RNA editing protein produce and secrete enhanced amounts of apo B48. These results are unexpected in view of the fact that endogenous apo B RNA is only slightly edited despite greater than about 50 percent of the edited form of the protein being secreted.

EXAMPLE 6

Isolation of cDNA encoding human small intestinal apo B mRNA editing protein

Samples of normal human adult tissues including small intestine were obtained from the National Disease Research Interchange or during the course of organ donor procurement, as approved by the Institutional Review Board of the University of Chicago Hospitals. Total or polyA+RNA was prepared using a standard technique described and used for reverse transcription-polymerase chain reaction (RT-PCR) amplification with two degenerate oligonucleotide primers (Teng et al., 1990). Those primers are shown below.

downstream primer, BFH-5-R
5'-CCANAGRTGNGGRTANCGNGG-CCARTG-3'     (SEQ ID NO:5)

upstream primer, BFH-3-F
5'-TGGTTYCTNWSNTGGWSNCCNTGY-3'     (SEQ ID NO:6)

where R=A or G; N=A,C,G or T; Y=C or T; W=A or T; S=C or G. Those primers were selected from a region spanning residues 86–174 of the rat intestinal apo B mRNA editing protein (Teng et al., 1993). 500 ng total RNA from normal human jejunum was annealed to 60 pmoles downstream primer (BFH-5-R) in 14.6 μl rTth buffer (10 mM Tris HCl, pH 8.3, 90 mM KCl) by heating to 75° C. for 5 min, cooling to room temperature and incubation at 42° C. for 10 min. RT was carried out at 60° C. for 15 min in 20 μl final volume rTth buffer supplemented with 1 mM MnCl$_2$, 200 tim dNTP's and 5u rTth (#N808-0097, Perkin-Elmer Cetus). PCR amplification was conducted by adding 8 μl chelating buffer (50% glycerol., 100 mM Tris HCl, pH 8.3, 1M KCl, 7.5 mM EGTA, 0.5% Tween-20), 6 μl 25 mM MgCl2, 60 pmoles upstream primer (BFH-3-F) and water to a final volume of 100 μl. 40 cycles of PCR were conducted with denaturation for 30 seconds at 95° C., annealing at 45° C. for 1 min and extension at 65° C. for 1.5 min.

A single PCR product of 267 bp was detected by agarose electrophoresis and cloned directly into plasmid pCRII (In Vitrogen, San Diego, Calif.). Three independent clones were sequenced on both strands (Teng & Davidson, 1992; Teng et al., 1993). Using the sequence so obtained, specific primers were then designed for selective amplification of the 5' and 3' ends of the cDNA with overlap at a convenient restriction site. The 5' end of the human cDNA was obtained using 2 μg poly A+RNA from human jejunum which was reverse transcribed at 42° C. for 30 min using 12.5 U avian myeloblastosis virus reverse transcriptase and 10 μM downstream (specific) primer (DSP1) 5'-TCCTCCAGCAGTGATAATACT CTG-3' (SEQ ID NO:7) (Edwards et al., 1991).

A modified oligonucleotide anchor 5'P-CAC-GAATTCACTATC GATTCTGGAACCTT-CAGAGG-NH3-3' (SEQ ID NO:8) (#K1800-1, Clontech, Calif.) was then ligated to the single stranded cDNA with 10 units T4 RNA ligase at 22° C. for 20 h as described by the supplier (Clontech) (Teng et al., 1990). PCR amplification was conducted using an anchor primer 5'-CTGGTTCGGCCCACCTCT-GAAGGTTCCAGAATCGATAG-3' (SEQ ID NO:9) (Clontech) and a nested antisense (specific) primer (DSP2) 5'-GCTCGAGGAGCTACGTAGAT-CACTAGAGTCA-3' (SEQ ID NO:10). PCR was conducted using Hot Tub DNA polymerase (Amersham, Arlington Heights, Ill.) with 35 cycles of 45 seconds denaturation at 94° C., 45 seconds annealing at 60° C. and 2 minutes extension at 72° C. with a final 7 minute extension after the last cycle. A single 374 bp PCR product was cloned into pCRII yielding 8 clones with inserts of which 3 were sequenced on both strands and shown to have the identical sequence.

The 3' end of the cDNA was independently obtained using 2 μg poly A+RNA from human jejunum to generate first strand cDNA synthesis which was primed using an adaptor primer 5'-GGCCACGCGT-CGACTA GTAC-(dT)17 (SEQ ID NO:11) (GIBCO-BRL, Gaithersburg, Md.) (Frohman et al., 1988). PCR amplification used an upstream (specific) primer (USP1) 5'-AGTCGACGTGTGACTCTAGTGATCTACG-3' (SEQ ID NO:12) and a downstream primer 5'-CUACUACUACUAGGCCAC GCGTCGACTAG-TAC-3' (SEQ ID NO:13). PCR conditions (30 cycles) were: denaturation at 94° C. for 30 seconds, annealing at 55° C. for 1 min and extension at 72° C. for 1.5 min. with a final extension time of 15 min. A single 537 bp PCR product was cloned into plasmid pCRII yielding 13 clones with inserts of which 5 were sequenced on both strands and found to have the identical sequence.

Both plasmids were digested with BamHI and SnaBI and a 410 bp fragment (369 bp of 5' cDNA and 41 bp of polylinker) removed from the 5' cDNA clone and ligated into the BamHI-SnaBI site of the 3' cDNA to yield the full length cDNA clone, pHEPR.

Using degenerate oligonucleotides from a region of the rat apo B RNA editing protein (REPR), a fragment of the human homolog was obtained which showed 75% nucleotide homology to REPR. The 5' and 3' ends of the human cDNA were subsequently obtained using sequence-specific primers and anchor-PCR. The DNA and deduced amino acid sequence are shown in FIG. 2.

The nucleotide sequence is 879 bp with a single open reading frame encoding a protein (HEPR) of 236 amino acids with a calculated molecular mass of about 28206 daltons. In vitro transcription/translation of the full length HEPR cDNA demonstrated a protein of approximately 27 kD in contrast to a smaller species (~25 kD) translated from REPR cDNA (Teng et al., 1993), findings consistent with the relative predicted size of the human and rat apo B mRNA editing proteins. The 3' untranslated region contains a consensus polyadenylation signal at nucleotides 858–863.

The nucleotide sequence demonstrates 76% overall identity to the rat sequence (Teng et al., 1993). A search of the National Center for Biotechnology Information peptide database showed only one protein with significant sequence similarity, namely REPR, with 69% amino acid identity and 79% similarity (Teng et al., 1993). HEPR was found to have a consensus N-glycosylation site (residue 57), phosphorylation sites for cAMP-dependent kinase (residue 68), casein kinase (residues 8 and 72) and protein kinase C (residues 3, 13, 47, 54, 72 and 196).

Additionally, as shown in FIG. 2, HEPR contains the zinc-binding motif His61, Cys93, Cys96 previously identified in the active site of other cytidine deaminases including REPR (Navaratnam et al., 1993). By contrast, while the carboxyl-terminus of REPR (residues 182-210) was found to contain a series of leucine residues in a heptad repeat suggestive of a leucine-zipper, this region was only 65% identical in HEPR and did not contain the same pattern of heptad leucine repeats.

There are several differences between the rat apo B mRNA editing protein and the human homolog. First, the overall species conservation between both the cDNA and predicted amino acid sequence is less than 70%. This is in contrast to the nucleotide conservation flanking the edited base in apo B mRNA where there is only one difference in 29 nucleotides between the rat and human sequence (Teng and Davidson, 1992). However, the conservation of the zinc-binding residues which coordinate to the active site of other cytidine deaminases (Navaratnam et al., 1993) suggests that the active site of REPR and HEPR are likely to be similar. Recent studies have demonstrated that zinc chelation irreversibly abolishes the ability of rat intestinal S100 extracts to edit a synthetic apo B RNA template, suggesting that REPR indeed functions as a zinc-dependent cytidine deaminase (Navaratnam et al., 1993).

A second distinguishing feature of HEPR was the absence of a carboxyl terminal leucine zipper, previously identified in REPR and postulated to be important in mediating potential interactions with other factors involved in apo B mRNA editing (Teng et al., 1993). The functional importance of this region of REPR was established following the abolition of in vitro apo B mRNA editing from oocytes injected with a truncated RNA which eliminated the carboxy-terminal 60 residues (Teng et al., 1993). Structural alterations to REPR in addition to the removal of residues spanning the putative leucine zipper may have contributed to the abolition of editing activity (Teng et al., 1993). In addition, that this motif in REPR would be considered atypical for a leucine zipper by virtue of the presence of proline residues and the overall absence of alpha helicity (Landschultz et al., 1988).

EXAMPLE 7

HEPR Editing Activity pHEPR was linearized in both sense and antisense orientations, transcribed and capped using T7 or SP6 RNA polymerase and the purified RNA dissolved in water. 600 ng of RNA was used in a 30 $\mu$l (final volume) in vitro translation reaction with nuclease-treated rabbit reticulocyte lysate (Gibco-BRL) as recommended by the manufacturer. Following in vitro translation, aliquots (5-10 $\mu$l) of the lysate were incubated in an in vitro editing assay using either rat or human synthetic apo B RNA templates in the presence of 20 $\mu$g of either chicken intestine or human liver S100 extracts (Giannoni et al., 1993) and the products quantitated by primer extension (Teng and Davidson, 1992; Teng et at., 1993). Separate aliquots of HEPR-RNA were translated in vitro using a methionine-deficient rabbit reticulocyte lysate in the presence of 35S-methionine and the products resolved by denaturing SDS-PAGE and detected by fluorography (Teng et al., 1993).

HEPR cDNA was transcribed and translated in vitro and aliquots of the translation reaction used in an in vitro apo B RNA editing assay. HEPR edits a synthetic apo B RNA template, prepared from either rat or human apo B cDNA, when complemented by chicken intestinal S100 extracts. The activity of HEPR is comparable to that of REPR studied under the same conditions with differences in the extent of conversion with different in vitro translation reactions. S100 extracts prepared from human liver also complemented the ability of HEPR to edit an apo B RNA template, although the editing activity of this mixture was lower (~2% UAA) than in mixtures supplemented with chicken intestinal S100 extracts (3-37% UAA). The ability of HEPR to edit an apo B RNA template varied in a dose-dependent manner but was strictly dependent upon the presence of a source of complementation activity, either chicken intestine or human liver S100 extracts. No editing was observed in reaction mixtures lacking a source of complementation activity.

EXAMPLE 8

RNA Blotting and Immunocytochemical Detection of HEPR

Human fetal and adult RNA samples (20 $\mu$g) were fractionated through formaldehyde-agarose gels and transferred to nylon membranes (Teng et al., 1990) and probed with a 32P-labeled 372 bp fragment corresponding to nucleotides 111-483 of pHEPR. Hybridization and washing stringencies were performed as described with the final wash at 42° C. in 0.1XSSC/0.1% SDS (Teng et al., 1990). The blots were exposed to XAR film for 4 days at $-80°$ C. with intensifying screens and reprobed without stripping with a 32P-labeled human glyceraldehyde-3-phosphate-dehydrogenase cDNA (ATCC#57090) under identical stringency.

An antipeptide antibody was generated against residues 17-36 (RIEPwEFnVFyDPRELRKEa) (SEQ ID NO: 18) of the rat editing protein (Research Genetics, Alabama) which contains 4 differences from the human sequence, shown in lower case. This antiserum reacted with both the rat and human editing protein on Western blots and in immunoprecipitation reaction and was used to localize HEPR in Bouin's fixed adult proximal human ileum. 5 $\mu$m sections were prepared on Vectabond-coated slides, treated (15 min) with 1% hydrogen peroxide, blocked (15 min) in 5% normal goat serum/3% bovine serum albumin (BSA) and reacted with anti-REPR IgG diluted to 4 $\mu$g/100 $\mu$l in PBS-0.3% Triton-1% BSA (30 min), all at room temperature. Control incubations contained peptide-absorbed anti-IgG. After washing, the slides were incubated with biotinylated goat anti-rabbit IgG and avidin-conjugated horseradish peroxidase (Vectaastain Elite, Vector Labs, Burlingame, Calif.) prior to color development and light counterstaining with hematoxylin (Inui et al., 1992).

RNA blots prepared from a variety of human fetal and adult tissues demonstrated a single transcript detectable only in the adult human small intestine. Transcript abundance appeared greater in the jejunum than in either duodenum or ileum. Both proximal and distal fetal human small intestinal RNA (14 weeks gestational age) fail to show a signal, suggesting that HEPR is developmentally regulated. No hybridization was detectable in adult or fetal liver.

Studies using an antipeptide antibody raised against a conserved region of REPR demonstrated an abundant reaction product throughout the upper virus absorptive region of adult small intestine with reaction in the intervillus regions but minimal reactivity in the crypts. Additionally, the immunoreactive product was apparent throughout the cell with occasional peri-and intranuclear localization. No reaction product was detectable with peptide-absorbed antiserum.

A further distinguishing feature to emerge between REPR and HEPR concerns the tissue distribution of these gene products. As assessed by Northern blotting, REPR mRNA was demonstrated as a variable sized transcript in several tissues in addition to the small intestine and liver, including spleen, lung, kidney and colon (Teng et al., 1993). The present results, using methodology of comparable sensitivity, demonstrates the presence of a single transcript detectable only in adult small intestine. These findings are not necessarily inconsistent with previous demonstration that edited apo B mRNA is detectable in multiple human fetal tissues, since HEPR may be expressed in these tissues at levels below the sensitivity of Northern blotting. Additionally, the demonstration that HEPR mRNA is most abundantly expressed in the adult small intestine is generally consistent with the previous finding that human fetal small intestinal apo B mRNA editing is developmentally regulated (Teng et al., 1990). Studies demonstrating that apo B mRNA editing is an intranuclear event are of interest in light of the immunocytochemical localization of HEPR throughout the absorptive enterocyte (Lau et al., 1991). These findings are not necessarily incompatible, since considerable evidence exists for shuttling of proteins between the nucleus and cytoplasm (Laskey and Dingwall, 1993).

No detectable hybridization signal for HEPR mRNA was found in either fetal or adult human liver, findings confirmed in nine additional normal adult human liver samples. These findings suggest a plausible explanation for the absence of apo B mRNA editing in the human liver. Previous studies showed that S100 extracts prepared from HepG2 cells, when mixed with oocyte homogenates expressing REPR, were competent to edit a synthetic apo B RNA template, thus suggesting that HepG2 extracts acquire editing competence through complementation with REPR (Teng et al., 1993). Support for this hypothesis can be found in the observation that normal adult and fetal human liver S100 extracts possess complementation activity for apo B RNA editing activity when mixed with REPR. Furthermore, HepG2 cells, transfected with REPR, demonstrated endogenous apo B mRNA editing and secreted apo B48 (Giannoni et al., 1993). Taken together, the evidence points to an absence of HEPR from human liver as the major component of the observation that this tissue does not edit endogenous apo B mRNA and fails to synthesize and secrete apo B48.

EXAMPLE 9

Human Liver Complementation Activity

A. Tissues and Extract Preparation and In Vitro Editing Assay

Human fetal liver was obtained from spontaneous or elective second trimester pregnancy terminations (provided by M. Verp, M. D. Section of Obstetrics and Gynecology, University of Chicago). Adult liver samples were obtained during the course of organ donor procurement (provided by T. Heffron, M. D. Department of Surgery, University of Chicago). The use of such tissue was approved by the Institutional Review Board of the University of Chicago Hospitals. Tissue was processed within 30 minutes of receipt and all steps were conducted at 0° C. Livers were finely minced and homogenized sequentially in a Dounce homogenizer with a type A and then a type B pestle, in Digham buffer A containing freshly added protease inhibitors, and centrifuged at 750×g in an SS34 rotor (DuPont-Sorvall Instruments) (Teng and Davidson, 1992).

The supernatant was adjusted by adding 0.11 volumes of Dignam buffer B and centrifuged at 100,000×g using an SW 55 Ti rotor (Beckman Instruments). S100 extracts were prepared from isolated enterocytes and cell culture monolayers (Teng and Davidson, 1992). Following dialysis and protein concentration determination, the extracts were stored at −80° C. in small aliquots.

Apo B RNA templates were generated from pGEM-CAA, a human apo B genomic fragment spanning nucleotides 6506-7335 and pRBF-CAA and a rat apo B cDNA fragment spanning nucleotides 6512-6982 cloned into pGEM 3Z or 4Z, respectively (Teng et al., 1990; Teng and Davidson, 1992). Plasmids were linearized and used to generate RNA templates of 361 or 428 nucleotides for rat and human apo B, respectively, using T7 or SP6 RNA polymerases (Teng et al., 1990; Teng and Davidson, 1992). Assays were conducted using 10 fmol of RNA substrate in the presence of the indicated amounts of oocyte homogenate and/or S100 extract and quantitative primer extension.

Extracts prepared from adult human liver, when mixed with oocyte extracts expressing REPR, edit greater than 50% of a synthetic rat apo B RNA template. Similar findings were demonstrated with two separate fetal (16 and 18 weeks gestational age) and three adult liver samples. Human liver extracts did not acquire editing activity upon mixing with chicken intestinal extracts, nor did they demonstrate endogenous apo B RNA editing activity. Thus, like chicken intestinal extracts, human liver extracts are ineffective alone in editing a synthetic apo B RNA template but complement the editing activity of oocyte extracts expressing REPR. In contrast to the findings with chicken intestinal extracts, coincubation of human liver extracts with rat intestinal extracts did not produce enhanced editing activity, suggesting, that differences exist in the abundance or composition of the editing complementation factors from chicken intestine and human liver.

Previous work established the minimum requisite RNA sequence information for in vitro editing of an apo B RNA template to be contained within 55 nucleotides flanking the edited base (Davies et al., 1989). In vitro editing of both rat and human apo B RNA substrates using constructs containing 361 or 428 nucleotides respectively flanking the edited base revealed the rat apo B RNA to be more efficiently edited than the comparable length human RNA template. These findings are consistent with previous work demonstrating differences in the efficiency of in vitro editing of rabbit and human apo B RNA templates by rabbit intestinal extracts (Garcia et al., 1992).

Studies were conducted to determine whether alterations in the proportion of REPR and the complementation factor(s), provided by either chicken intestine or human liver S100 extracts, changed the efficiency of in vitro editing of either the rat or human apo B RNA templates. Either REPR or tissue S100 extracts were added in increasing amounts with the other component being held constant. The data (See FIG. X) show that an optimal ratio of REPR and either tissue complementation factor(s) is required for in vitro editing of both rat and human apo B RNA templates with excess of either extract inhibiting the reaction. Apo B mRNA editing activity could be restored, following inhibition, to incubation mixtures containing excess chicken intestinal or human liver S100 extract following the further addition of oocyte homogenate expressing REPR. Complementary findings were encountered in restitution experiments (using chicken intestinal or human liver S100 extract) conducted following inhibition with excess oocyte extract.

B. Transfection of HepG2 Cells and Analysis of REPR Expression

Studies were conducted to establish the functional expression of REPR in vivo to establish the biological relevance of apo B mRNA editing factor(s) in human liver.

A full length cDNA containing the open reading frame of REPR as a Sal I- Not I fragment was blunt ended with the Klenow fragment of DNA polymerase I and cloned into the pCMV 4 expression vector, provided by D. W. Russell, University of Texas, Southwestern Medical Center (Andersson et al., 1989). HepG2 cells were obtained from ATCC (#HB 8065) and maintained in minimum essential medium (GIBCO #320-1090 PK) supplemented with 0.1 mM nonessential amino acids, 2 mM L-glutamine, 1 mM sodium pyruvate, 50 u/ml penicillin, 50 µg/ml gentamicin and 50 µg/ml streptomycin in 10% fetal bovine serum (GIBCO). Parallel dishes of HepG2 cells were plated at $1 \times 10^6$ cells per 100 mm dish and transfected with 10 µg supercoiled DNA encoding either REPR or pGEM (control), together with 1 µg pSV-2 Neo, using calcium phosphate precipitation (Ausubel et al., 1987). After incubation for 16-20 h, the cells were washed extensively with phosphate buffered saline but were not subjected to glycerol shock. Stable transfectants were selected in media supplemented with 800 µg/ml G418 (GIBCO).

Following an initial round of selection, isolated colonies were identified and confluent monolayers prepared from cells maintained in media supplemented with 400 µg/ml G418. Media was collected from stable transfectants following a 16 h labeling of T 75 flasks with 150 µCi/ml Tran 35S-label (ICN, Costa Mesa, Calif.) and lipoproteins of density less than 1.21 g/ml floated by ultracentrifugation (Spring et al., 1992). After exhaustive dialysis, aliquots of the lipoprotein fraction were immunoprecipitated with polyclonal anti-human apo B antisera and resolved by denaturing 5% SDS-polyacrylamide gel electrophoresis (Teng et al., 1990).

Media from radiolabeled cells was examined by ultracentrifugation and immunoprecipitation, revealing a truncated apo B immunoreactive protein with the mobility of apo B48 which represented approximately 30% of total immunoreactive apo B. Extracts prepared from these cells were found to have in vitro editing ability for both rat and human apo B RNA templates, an activity enhanced by the addition of chicken intestinal extracts. Taken together, these data suggest that REPR is expressed and functionally active following transfection into HepG2 cells.

Endogenous apo B mRNA from both REPR- and control transfected-HepG2 cells was analzyed using two different strategies. In the first approach, apo B mRNA was amplified by RT-PCR using downstream-primed first strand cDNA synthesis from a region present in both 7 and 14 Kb apo B mRNA species, which results in the unselected amplification of total apo B mRNA's (Powell et al., 1987).

Total RNA was extracted from groups of transfected HepG2 cells (either REPR or pGEM) (Teng et al., 1990). Aliquots of total RNA were treated with DNAse RQ1 (Promega, Wis.), extracted with phenol-chloroform, precipitated with ethanol and resuspended in water. Total apo B mRNA was amplified by RT-PCR (Giannoni et al., 1993). Briefly, reverse transcription was performed at 70° C. for 15 minutes in a final volume of 20 ml RT buffer, containing 10 mM TrisHCl pH 8.3, 90 mM KCl, 1 mM $MnCl_2$, 200 mM each dNTP, 30–60 pmoles PCR 10B (see below, downstream primer for primer pair A), 5u rTth (#N808-0097, Perkin Elmer-Cetus, Conn.). Following reverse transcription, 80 µl (final volume) of PCR buffer was added to each tube, containing 8 µl chelating buffer (50% v/v glycerol, 100 mM Tris HCl pH 8.3, 1M KCl, 7.5 mM EGTA, 0.5% Tween 20), 6 µl 25 mM $MgCl2$ (1.5 mM final concentration) and 30 to 60 pmoles PCR 5 in 66 µl of $H_2O$. After 3 minutes at 95° C., PCR was performed for 30 cycles of: 30 seconds at 95° C., 1 minute at 55° C., 1.5 minutes at 72° C.

A final 10 minute extension at 72° C. was added after the last cycle. For each RNA sample a negative control was run to check for DNA contamination using rTth and leaving the sample on ice during reverse transcription (RT−). One tenth of the reaction material was analyzed by 2% agarose electrophoresis to confirm the expected amplification product of 283 base pairs. A representative example so analyzed from REPR-transfected HepG2 cells revealed approximately 15% of total apo B mRNA to be edited.

The possibility was then explored that HepG2 cells, transfected with REPR, contain a shorter species of apo B mRNA which might be differentially edited. An analysis was undertaken in which the 7 Kb mRNA species was selectively amplified from both control- and REPR-transfected HepG2 cells using a brief oligo-dT primed first strand cDNA synthesis reaction followed by amplification using primers specific for the region 5-prime to the predicted polyadenylation sites in human apo B mRNA (Powell et al., 1987; Chen et al., 1991; Giannoni et al., 1993).

To amplify the 7 Kb transcript, total RNA was reverse transcribed using 60 pmoles oligo-dT (12–18 mer, Pharmacia #00103788) to prime first strand cDNA synthesis as follows: a mix containing DNA-sed RNA, RT buffer, $H_2O$ and oligo-dT primers was heated at 75° C. for 5 minutes to denature the RNA, cooled to room temperature and anneal. ed for 10 minutes at 42° C. Reverse transcription was performed at 60° C. for 1 minute after adding rTth, MnCl2 and dNTP's as above. The cDNA thus generated was then amplified using PCR5 and PCR10B (primer pair A).

Primer Pair A [apo B cDNA product of 283 base pairs]
PCR 5 (5' CTGAATTCATTCAATTG-GGAGAGACAAG3', 5' at 6504)    (SEQ ID NO:14)

PCR 10B (5'CACGGATATGATAGTGCTCAT3', 5'at 6787)    (SEQ ID NO:15)

Control reactions were reverse transcribed with oligo-dT and PCR amplified using PCR5 and PCR-14 (primer pair B) to insure that no 14 Kb transcript had been reverse transcribed (as evidenced by the absence of a product of 775 base pairs).

Primer Pair B [apo B cDNA product of 775 base pairs]

PCR 5 (5' CTGAATTCATTCAATTG-GGAGAGACAAG3', 5' at 6504) (SEQ ID NO:16)

PCR-14 (5' CTTGTTGTAGGACATTGCTTAGCT 3, 5' at 7278) (SEQ ID NO:17)

For each RNA sample a PCR was run without reverse transcription using PCR5 and PCR10B to exclude genomic DNA or PCR product contamination (RT−). Reaction products were then purified and analyzed by primer extension (Teng and Davidson, 1992; Giannoni et al., 1993).

A 7 Kb apo B transcript was detectable in both control- and REPR-transfected HepG2 cells. Analysis of the RT-PCR products by primer extension revealed enhanced editing (55–57%) of the 7 Kb apo B mRNA species in REPR-transfected HepG2 cells relative to total apo B mRNA (~15%). No detectable editing of the 7 Kb apo B mRNA was demonstrated in control-transfected HepG2 cells. However, the presence of a species of apo B mRNA which undergoes selective editing in REPR-transfected cells suggests the possibility that apo B48 production from these cells is linked to the production of a discreet population of edited apo B mRNA. The enhanced editing observed in these studies is over the editing activity observed in Example 5.

While the compositions and methods of this invention have been described in terms of preferred embodiments, it will be apparent to those of skill in the art that variations can be applied to the composition, process and in the steps or in the sequence of steps of the process described herein without departing from the concept, spirit and scope of the invention.

REFERENCES

The references listed below as well as other references recited herein are incorporated herein by reference to the extent that they supplement, explain, provide a background for or teach methodology, techniques and/or compositions employed herein.

Andersson et al., *J. Biol. Chem* (1989) 264:8222
Ausubel et al., *Current Protocols in Mol. Biol.* (1987) p.9.1
Baum et al., *J. Biol. Chem.* (1990) 265:19263
Beisegel et al., *Nature* (1989) 341:162
Bostrom et al., *J. Bio. Chem.* (1990) 265:22446–22452
Bostrom et al., *J. Biol. Chem.* (1989) 264:15701
Bradford, *Anal. Biochem.* (1976) 72:248–254
Breslow, *Physiol. Rev.* (1988)68:85–132
Cattaneo, *Ann. Rev. Genet.* (1991) 25:71
Chan, *J. Biol. Chem.* (1992) 267:25621.
Chan et al., *Biochem. Biophys. Res. Comm.* (1985) 133:248
Chen et al., *J. Biol. Chem.* (1990) 265:6811–6816
Chen et al., *Science* (1987) 238:362–366
Chen et al., *Science* (1991) 238:363
Chen et al., *J. Biol. Chem.* (1986) 261:12918
Cladaras et al., *EMBO J.* (1986) 5:3495
Coleman et al., *J. Lipid Res.* (1988) 28:33
Davidson et al., *J. Lipid Res.* (1988) 29:1511
Davidson et at., *J. Biol. Chem.* (1988) 263:13482
Davidson et al., *Mol. Endocrinol.* (1990) 4:779
Davidson et al., *J. Lipid Res.* (1990) 31:899
Davies et al., *J. Biol. Chem.* (1989) 264:13395
Demmer et al., *Proc. Natl. Acad. Sci. USA* (1986) 83:8102
Dignam et al., *Nucl. Acids Res.* (1983) 11:1475–1489
Driscoll and Casanova, *J. Biol. Chem.* (1990) 265:21401–21403
Driscoll et at., *Cell* (1989) 58:519–525
Edwards et al., *Nucleic Acids Res.* (1991) 19:5227.
Felgner and Rhodes, *Nature* (1991) 349:35 1–352
Ferutti and Tanzi, *Crit. Rev. Ther. Drug Carrier Syst.* (1986) 2:117–136
Frohman and Martin, *Cell* (1989) 56:145–147
Frohman et al., *Proc. Natl. Acad. Sci. USA* (1988) 85:8998
Gabizon et al., *Cancer Res.* (1990) 50:6371–78
Garcia et al., *Arteriosclerosis* (1991) 12:172–179
Giannoni et al., *J. Biol. Chem.* (1993) In Press.
Greeve et al., *Nucleic Acids Res.* (1991) 19:3569
Greeve et al., *J. Lipid Res.* (1993) 34:1367
Hardman et al., *Biochemistry* (1987) 26:5478
Harris et al, *J. Biol. Chem* (1993) 268:7382
Hatzoglou et al., *J. Biol. Chem.* (1990) 28:17285–17293
Herz et al., *EMBO J.* (1988) 7:4119
Higuchi et al., *J. Lipid Res.* (1992) 33:1753
Hodges and Scott, *Trends Biochem. Sci.* (1992) 17:77–81
Hodges et al., *J. Nucl. Acids* (1991) 19:1197–1201
Hopkins et al., *Development* (1987) 100:83
Hospattankar et al., *Biochem. Biophys. Res. Comm.* (1987) 148:279
Huber et al., *Proc. Natl. Acad. Sci. USA* (1991) 88:8039–8043
Innerarity et al., *J. Clin. Invest.* (1987) 80:1794
Inui et al., *J. Lipid. Res.* (1992) 33:1843
Jiao et al., *J. Lipid Res.* (1990) 31:695
Jiao et al., *Arteriosclerosis and Thrombosis* (1991) 11:1424a
Johnson et al., *Biochem. Biophys. Res. Comm.* (1993) 195:1204
Kayano et al., *J. Biol. Chem.* (1990) 265:13276–13282
Knott et al., *Nature* (1986) 323:734
Kowal et al., *Proc. Natl. Acad. Sci. USA* (1989) 86:5810
Kyte & Doolittle, *J. Mol. Biol.* (1982) 157:105
Landschultz et al., *Science* (1988) 240:1759
Laskey and Dingwall, *Cell* (1993) 74:585
Lau et al., *Nucl. Acids Res.* (1990) 18:5817
Lau et al., *J. Biol. Chem.* (1991) 266:20550
Lau et al., *Nucleic Acids Res.* (1991) 18:5817
Law and Scott, *J. Lipid Res.* (1990) 31:1109
Li et al., *J. Lipid Res.* (1988) 29:245
Ludwig et al., *DNA* (1987) 6:363
Luo et al., *J. Mol. Biol.* (1986) 187:325
Mansour, *GATA* (1990) 8:219–227
McCormick, *Methods Enzymol.* (1987) 151:445–449
Mehrabian et al., *Somatic Cell and Molecular Genetics* (1986) 12:245
Moore et al., *J. Biol. Chem.* (1993) 268:2288
Navaratnam et al., *Nucleic Acids Res.* (1991) 19:1741
Navaratnam et al., *Proc. Natl. Acad. Sci. USA*, 90:222
Navaratnam et al., *J. Biol. Chem.* (1993) 268:20709
O'Halloran, *Science* (1993) 261:715
Pease et al., *J. Biol. Chem.* (1990) 265:553
Powell et al., *Cell* (1987) 50:831–840
Ranade, *J. Clin. Pharmacol.* (1989)29(8):685–694
Seishima et al., *J. Lipid Res.* (1991) 32:941
Shah et al., *J. Biol. Chem.* (1991) 266:16301–16304
Smith et al., *Proc. Natl. Acad. Sci. USA* (1991) 88:1489–1493
Spring et al., *J. Lipid. Res.* (1992) 33:233

Sollner-Webb, *Curr. Op. Cell. Bio.* (1991) 3:1056
Sumikawa et al., *Embo. J.* (1984) 3:2291–2294
Sutter and Moss, *Proc. Natl. Acad. Sci. USA* (1992)89:10847–10851
Teng et al., *Biochem. Biophys. Res. Comm.* (1990) 173:74
Teng et al., *J. Biol. Chem.* (1990) 265:20616
Teng and Davidson, *Science* (1993) 260:1816
Teng and Davidson, *Arteriosclerosis and Thrombosis* (1991) 11:1402a
Teng and Davidson, *J. Biol. Chem.* (1992) 267:21265
Walsh et al., *Proc. Natl. Acad. Sci. USA* (1992) 89:7257–7261
Weatherall, *Nature* (1991)349:275–276
Wu et al., *J. Biol. Chem.* (1990) 265:12312
Wu et al., *J. Biol. Chem.* (1989) 29:16985
Yang et al., *Nature* (1986) 323:738
Yang et al., *Proc. Natl. Acad. Sci. USA* (1990) 87:5523
Zwiebel et al., *Science* (1989) 243:220

---

What is claimed is:

1. An isolated polynucleotide that encodes a human apo B RNA editing protein having an apparent molecular weight of from about 25 to about 28 kilodaltons as determined by polyacrylamide gel electrophoresis.

2. The polynucleotide according to claim 1 wherein said protein comprises the amino acid residue sequence of SEQ ID NO:4.

3. The polynucleotide according to claim 1 wherein said polynucleotide is a cDNA molecule.

4. The polynucleotide according to claim 1 wherein said polynucleotide comprises the DNA sequence of SEQ ID NO:3 from about nucleotide position 23 to about nucleotide position 730.

5. The polynucleotide according to claim 1 wherein said polynucleotide comprises the DNA sequence of SEQ ID NO:3.

6. An expression vector comprising a polynucleotide in accordance with claim 1.

7. The vector according to claim 6 wherein said vector is an adenovirus vector construct.

8. A process of preparing a human Apo B RNA editing protein comprising the steps of:
  (a) transfecting a cell with an expression vector in accordance with claim 6 to produce a transformed cell; and
  (b) maintaining said transformed cell under biological conditions sufficient for expression of said protein.

9. A transfected cell comprising the expression vector of claim 6.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 879 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CCACGCGTCC  GAGGAAGGAG  TCCAGAGACA  CAGAGAGCAA  GATGAGTTCC  GAGACAGGCC      60
CTGTAGCTGT  TGATCCCACT  CTGAGGAGAA  GAATTGAGCC  CCACGAGTTT  GAAGTCTTCT     120
TGACCCCCGG  GAACTTCGGA  AAGAGACCTG  TCTGCTGTAT  GAGATCAACT  GGGGAGGAAG     180
GCACAGCATC  TGGCGACACA  CGAGCCAAAA  CACCAACAAA  CACGTTGAAG  TCAATTTCAT     240
AGAAAAATTT  ACTACAGAAA  GATACTTTTG  TCCAAACACC  AGATGCTCCA  TTACCTGGTT     300
CCTGTCCTGG  AGTCCCTGTG  GGGAGTGCTC  CAGGGCCATT  ACAGAATTTT  TGAGCCGATA     360
CCCCCATGTA  ACTCTGTTTA  TTTATATAGC  ACGGCTTTAT  CACCACGCAG  ATCCTCGAAA     420
TCGGCAAGGA  CTCAGGCAGC  TTATTAGCAG  CGGTGTTACT  ATCCAGATCA  TGACGGAGCA     480
AGAGTCTGGC  TACTGCTGGA  GGAATTTTGT  CAACTACTCC  CCTTCGAATG  AAGCTCATTG     540
GCCAAGGTAC  CCCCATCTGT  GGGTGAGGCT  GTACGTACTG  GAACTCTACT  GCATCATTTT     600
AGGACTTCCA  CCCTGTTTAA  ATATTTAAG   AAGAAAACAA  CCTCAACTCA  CGTTTTCAC      660
GATTGCTCTT  CAAAGCTGCC  ATTACCAAAG  GCTACCACCC  CACATCCTGT  GGGCCACAGG     720
GTTGAAATGA  CTTCTGGGAG  TTGGGGATGG  ATGAAATGAC  TCCTTGTATG  TCTTGACAGC     780
AGCAATTGAT  TACCCACTAA  AGAGCGACTG  CCACAAGGAA  TCTAGAAGTC  GAAAAAAAAA     840
AAAAAAAAAA  AAAAAAAAAA  AAAAAAAAAA  AAAAAAAA                              879
```

( 2 ) INFORMATION FOR SEQ ID NO:2:

( i ) SEQUENCE CHARACTERISTICS:
        ( A ) LENGTH: 229 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met  Ser  Ser  Glu  Thr  Gly  Pro  Val  Ala  Val  Asp  Pro  Thr  Leu  Arg  Arg
 1              5                        10                         15

Arg  Ile  Glu  Pro  His  Glu  Phe  Glu  Val  Phe  Phe  Asp  Pro  Arg  Glu  Leu
                20                        25                         30

Arg  Lys  Glu  Thr  Cys  Leu  Leu  Tyr  Glu  Ile  Asn  Trp  Gly  Gly  Arg  His
                 35                        40                         45
```

```
          Ser  Ile  Trp  Arg  His  Thr  Ser  Gln  Asn  Thr  Asn  Lys  His  Val  Glu  Val
               50                      55                       60

Asn  Phe  Ile  Glu  Lys  Phe  Thr  Thr  Glu  Arg  Tyr  Phe  Cys  Pro  Asn  Thr
          65                      70                       75                            80

Arg  Cys  Ser  Ile  Thr  Trp  Phe  Leu  Ser  Trp  Ser  Pro  Cys  Gly  Glu  Cys
                         85                       90                            95

Ser  Arg  Ala  Ile  Thr  Glu  Phe  Leu  Ser  Arg  Tyr  Pro  His  Val  Thr  Leu
                         100                      105                      110

Phe  Ile  Tyr  Ile  Ala  Arg  Leu  Tyr  His  His  Ala  Asp  Pro  Arg  Asn  Arg
                    115                       120                      125

Gln  Gly  Leu  Arg  Asp  Leu  Ile  Ser  Ser  Gly  Val  Thr  Ile  Gln  Ile  Met
               130                      135                      140

Thr  Glu  Gln  Glu  Ser  Gly  Tyr  Cys  Trp  Arg  Asn  Phe  Val  Asn  Tyr  Ser
          145                      150                      155                           160

Pro  Ser  Asn  Glu  Ala  His  Trp  Pro  Arg  Tyr  Pro  His  Leu  Trp  Val  Arg
                              165                      170                           175

Leu  Tyr  Val  Leu  Glu  Leu  Tyr  Cys  Ile  Ile  Leu  Gly  Leu  Pro  Pro  Cys
                         180                      185                      190

Leu  Asn  Ile  Leu  Arg  Arg  Lys  Gln  Pro  Gln  Leu  Thr  Phe  Phe  Thr  Ile
                    195                      200                      205

Ala  Leu  Gln  Ser  Cys  His  Tyr  Gln  Arg  Leu  Pro  Pro  His  Ile  Leu  Trp
               210                      215                      220

Ala  Thr  Gly  Leu  Lys
          225
```

( 2 ) INFORMATION FOR SEQ ID NO:3:

( i ) SEQUENCE CHARACTERISTICS:
        ( A ) LENGTH: 879 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 23..730

( x i ) SEQUENCE DESCRIPTION: SEQ ID NO:3:

```
TGAATTCGTG GGACAGAGCA CC ATG ACT TCT GAG AAA GGT CCT TCA ACC GGT           52
                         Met Thr Ser Glu Lys Gly Pro Ser Thr Gly
                          1               5                  10

GAC CCC ACT CTG AGG AGA AGA ATC GAA CCC TGG GAG TTT GAC GTC TTC           100
Asp Pro Thr Leu Arg Arg Arg Ile Glu Pro Trp Glu Phe Asp Val Phe
             15                  20                  25

TAT GAC CCC AGA GAA CTT CGT AAA GAG GCC TGT CTG CTC TAC GAA ATC           148
Tyr Asp Pro Arg Glu Leu Arg Lys Glu Ala Cys Leu Leu Tyr Glu Ile
         30                  35                  40

AAG TGG GGC ATG AGC CGG AAG ATC TGG CGA ACG TCA GGC AAA AAC ACC           196
Lys Trp Gly Met Ser Arg Lys Ile Trp Arg Thr Ser Gly Lys Asn Thr
             45                  50                  55

ACC AAT CAC GTG GAA GTT AAT TTT ATA AAA AAA TTT ACG TCA GAA AGA           244
Thr Asn His Val Glu Val Asn Phe Ile Lys Lys Phe Thr Ser Glu Arg
 60                  65                  70

GAT TTT CAC CCA TCC ATC AGC TGC ACC ATC ACC TGG TCC TTG TCC TGG           292
Asp Phe His Pro Ser Ile Ser Cys Thr Ile Thr Trp Ser Leu Ser Trp
 75                  80                  85                  90

AGT CCC TGC TGG GAA TGC TCC CAG GCT ATT AGA GAG TTT CTG AGT CGG           340
Ser Pro Cys Trp Glu Cys Ser Gln Ala Ile Arg Glu Phe Leu Ser Arg
                 95                 100                 105
```

| | | | | | | | | | | | | | | | | |
|---|---|---|---|---|---|---|---|---|---|---|---|---|---|---|---|---|
| CAC | CCT | GGT | GTG | ACT | CTA | GTG | ATC | TAC | GTA | GCT | CGG | CTT | TTT | TGG | CAC | 388 |
| His | Pro | Gly | Val | Thr | Leu | Val | Ile | Tyr | Val | Ala | Arg | Leu | Phe | Trp | His | |
| | | 110 | | | | | 115 | | | | | | 120 | | | |
| ATG | GAT | CAA | CAA | AAT | CGG | CAA | GGT | CTC | AGG | GAC | CTT | GTT | AAC | AGT | GGA | 436 |
| Met | Asp | Gln | Gln | Asn | Arg | Gln | Gly | Leu | Arg | Asp | Leu | Val | Asn | Ser | Gly | |
| | | 125 | | | | 130 | | | | | 135 | | | | | |
| GTA | ACT | ATT | CAG | ATT | ATG | AGA | GCA | TCA | GAG | TAT | TAT | CAC | TGC | TGG | AGG | 484 |
| Val | Thr | Ile | Gln | Ile | Met | Arg | Ala | Ser | Glu | Tyr | Tyr | His | Cys | Trp | Arg | |
| | 140 | | | | | 145 | | | | | | 150 | | | | |
| AAT | TTT | GTC | AAC | TAC | CCA | CCT | GGG | GAT | GAA | GCT | CAC | TGG | CCA | CAA | TAC | 532 |
| Asn | Phe | Val | Asn | Tyr | Pro | Pro | Gly | Asp | Glu | Ala | His | Trp | Pro | Gln | Tyr | |
| 155 | | | | | 160 | | | | | 165 | | | | | 170 | |
| CCA | CCT | CTG | TGG | ATG | ATG | TTG | TAC | GCA | CTG | GAG | CTG | CAC | TGC | ATA | ATT | 580 |
| Pro | Pro | Leu | Trp | Met | Met | Leu | Tyr | Ala | Leu | Glu | Leu | His | Cys | Ile | Ile | |
| | | | | 175 | | | | | 180 | | | | | 185 | | |
| CTA | AGT | CTT | CCA | CCC | TGT | TTA | AAG | ATT | TCA | AGA | AGA | TGG | CAA | AAT | CAT | 628 |
| Leu | Ser | Leu | Pro | Pro | Cys | Leu | Lys | Ile | Ser | Arg | Arg | Trp | Gln | Asn | His | |
| | | | 190 | | | | | 195 | | | | | 200 | | | |
| CTT | ACA | TTT | TTC | AGA | CTT | CAT | CTT | CAA | AAC | TGC | CAT | TAC | CAA | ACG | ATT | 676 |
| Leu | Thr | Phe | Phe | Arg | Leu | His | Leu | Gln | Asn | Cys | His | Tyr | Gln | Thr | Ile | |
| | | 205 | | | | | 210 | | | | | 215 | | | | |
| CCG | CCA | CAC | ATC | CTT | TTA | GCT | ACA | GGG | CTG | ATA | CAT | CCT | TCT | GTG | GCT | 724 |
| Pro | Pro | His | Ile | Leu | Leu | Ala | Thr | Gly | Leu | Ile | His | Pro | Ser | Val | Ala | |
| | 220 | | | | | 225 | | | | | 230 | | | | | |
| TGG | AGA | TGAATAGGAT | GATTCCGTGT | GTGTACTGAT | TCAAGAACAA | GCAATGATGA | | | | | | | | | | 780 |
| Trp | Arg | | | | | | | | | | | | | | | |
| 235 | | | | | | | | | | | | | | | | |

CCCACTAAAG AGTGAATGCC ATTTAGAATC TAGAAATGTT CACAAGGTAC CCCAAAACTC 840

TGTAGCTTAA ACCAACAATA AATATGTATT ACCTCTGGC 879

( 2 ) INFORMATION FOR SEQ ID NO:4:

( i ) SEQUENCE CHARACTERISTICS:
( A ) LENGTH: 236 amino acids
( B ) TYPE: amino acid
( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Thr | Ser | Glu | Lys | Gly | Pro | Ser | Thr | Gly | Asp | Pro | Thr | Leu | Arg | Arg |
| 1 | | | | 5 | | | | | 10 | | | | | 15 | |
| Arg | Ile | Glu | Pro | Trp | Glu | Phe | Asp | Val | Phe | Tyr | Asp | Pro | Arg | Glu | Leu |
| | | | 20 | | | | | 25 | | | | | 30 | | |
| Arg | Lys | Glu | Ala | Cys | Leu | Leu | Tyr | Glu | Ile | Lys | Trp | Gly | Met | Ser | Arg |
| | | 35 | | | | | 40 | | | | | 45 | | | |
| Lys | Ile | Trp | Arg | Thr | Ser | Gly | Lys | Asn | Thr | Thr | Asn | His | Val | Glu | Val |
| | 50 | | | | | 55 | | | | | 60 | | | | |
| Asn | Phe | Ile | Lys | Lys | Phe | Thr | Ser | Glu | Arg | Asp | Phe | His | Pro | Ser | Ile |
| 65 | | | | | 70 | | | | | 75 | | | | | 80 |
| Ser | Cys | Thr | Ile | Thr | Trp | Ser | Leu | Ser | Trp | Ser | Pro | Cys | Trp | Glu | Cys |
| | | | 85 | | | | | 90 | | | | | 95 | | |
| Ser | Gln | Ala | Ile | Arg | Glu | Phe | Leu | Ser | Arg | His | Pro | Gly | Val | Thr | Leu |
| | | | 100 | | | | | 105 | | | | | 110 | | |
| Val | Ile | Tyr | Val | Ala | Arg | Leu | Phe | Trp | His | Met | Asp | Gln | Gln | Asn | Arg |
| | | 115 | | | | | 120 | | | | | 125 | | | |
| Gln | Gly | Leu | Arg | Asp | Leu | Val | Asn | Ser | Gly | Val | Thr | Ile | Gln | Ile | Met |
| | 130 | | | | | 135 | | | | | 140 | | | | |
| Arg | Ala | Ser | Glu | Tyr | Tyr | His | Cys | Trp | Arg | Asn | Phe | Val | Asn | Tyr | Pro |
| 145 | | | | | 150 | | | | | 155 | | | | | 160 |

```
Pro Gly Asp Glu Ala His Trp Pro Gln Tyr Pro Pro Leu Trp Met Met
                165             170                 175

Leu Tyr Ala Leu Glu Leu His Cys Ile Ile Leu Ser Leu Pro Pro Cys
            180             185             190

Leu Lys Ile Ser Arg Arg Trp Gln Asn His Leu Thr Phe Phe Arg Leu
            195             200             205

His Leu Gln Asn Cys His Tyr Gln Thr Ile Pro Pro His Ile Leu Leu
            210             215             220

Ala Thr Gly Leu Ile His Pro Ser Val Ala Trp Arg
225             230             235
```

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

CCANAGRTGN GGRTANCGNG GCCARTG 27

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

TGGTTYCTN W SNTGG W SNCC NTGY 24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TCCTCCAGCA GTGATAATAC TCTG 24

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CACGAATTCA CTATCGATTC TGGAACCTTC AGAGG 35

(2) INFORMATION FOR SEQ ID NO:9:

(i) SEQUENCE CHARACTERISTICS:
        (A) LENGTH: 38 base pairs
        (B) TYPE: nucleic acid
        (C) STRANDEDNESS: single ( D ) TOPOLOGY: linear ( i i ) MOLECULE TYPE: DNA ( x i ) SEQUENCE DESCRIPTION: SEQ ID NO:9:

CTGGTTCGGC CCACCTCTGA AGGTTCCAGA ATCGATAG    38

( 2 ) INFORMATION FOR SEQ ID NO:10:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GCTCGAGGAG CTACGTAGAT CACTAGAGTC A    31

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

GGCCACGCGT CGACTAGTAC    20

( 2 ) INFORMATION FOR SEQ ID NO:12:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

AGTCGACGTG TGACTCTAGT GATCTACG    28

( 2 ) INFORMATION FOR SEQ ID NO:13:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

CUACUACUAC UAGGCCACGC GTCGACTAGT AC    32

( 2 ) INFORMATION FOR SEQ ID NO:14:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

CTGAATTCAT TCAATTGGGA GAGACAAG    28

(2) INFORMATION FOR SEQ ID NO:15:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:15:

CACGGATATG ATAGTGCTCA T                                                      21

(2) INFORMATION FOR SEQ ID NO:16:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:16:

CTGAATTCAT TCAATTGGGA GAGACAAG                                               28

(2) INFORMATION FOR SEQ ID NO:17:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:17:

CTTGTTGTAG GACATTGCTT AGCT                                                   24

(2) INFORMATION FOR SEQ ID NO:18:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:18:

Arg Ile Glu Pro Trp Glu Phe Asn Val Phe Tyr Asp Pro Arg Glu Leu
               5                  10                  15
Arg Lys Glu Ala
          20